US 6,391,638 B1
United States Patent
Shaaltiel

(10) Patent No.: US 6,391,638 B1
(45) Date of Patent: *May 21, 2002

(54) CELL/TISSUE CULTURING DEVICE AND METHOD

(75) Inventor: Yoseph Shaaltiel, Beit Hillel (IL)

(73) Assignee: Metabogal, Ltd., Kiryat Shemona (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/246,600

(22) Filed: Feb. 8, 1999

Related U.S. Application Data

(63) Continuation-in-part of application No. PCT/IL97/00316, filed on Sep. 26, 1997.

(30) Foreign Application Priority Data

Sep. 26, 1996 (IL) ................................................ 119310

(51) Int. Cl.[7] ................................................ C12N 5/00
(52) U.S. Cl. ................ 435/383; 435/289.1; 435/292.1; 435/296.1; 435/304.1
(58) Field of Search ............................ 435/383, 289.1, 435/292.1, 296.1, 304.1

(56) References Cited

U.S. PATENT DOCUMENTS

| 467,993 A | 2/1892 | Jorgensen et al. |
| 2,147,271 A | 2/1939 | Schwarz et al. |
| 2,341,259 A | 2/1944 | Baldwin |
| 2,836,434 A | 5/1958 | Heden |
| 3,201,327 A | 8/1965 | Beck |
| 3,468,520 A | 9/1969 | Duryea et al. |
| 3,504,185 A | 3/1970 | Zweig et al. |
| 3,540,700 A | 11/1970 | Freedman et al. |
| 3,705,082 A | 12/1972 | Hondermarck et al. |
| 3,743,582 A | 7/1973 | Kitai et al. |
| 3,793,154 A | 2/1974 | Efthymiou |
| 3,806,423 A | 4/1974 | Karrenbauer et al. |
| 3,950,227 A | 4/1976 | Efthymiou |
| 4,179,339 A | 12/1979 | Sogi et al. |
| 4,228,243 A | 10/1980 | Iizuka |
| 4,328,317 A | 5/1982 | Prentice et al. |

(List continued on next page.)

FOREIGN PATENT DOCUMENTS

| DE | 26 54 725 | 6/1977 |
| EP | 0 200 792 | 11/1986 |
| EP | 0 343 885 | 11/1989 |
| EP | 0 350 723 | 1/1990 |
| GB | 1 053 848 | 1/1967 |
| GB | 2 202 549 | 9/1988 |
| HU | 2002002 | 4/1990 |
| SU | 1 687 604 | 1/1989 |
| WO | WO88/00234 | 1/1988 |

OTHER PUBLICATIONS

Rompp Lexikon Biotechnologies, 1992, pp. 6–7.

Primary Examiner—David A. Redding
(74) Attorney, Agent, or Firm—Alston & Bird LLP

(57) ABSTRACT

A disposable device and method for axenically culturing and harvesting cells and/or tissue in consecutive cycles. The device consists of a sterilisable disposable container which may be partially filled with a suitable sterile biological cell and/or tissue culture medium. The container has means for removing excess air and/or waste gases therefrom, and means for introducing inoculant and/or culture medium and/or additives therein. A reusable harvesting means enables harvesting of at least a portion of the medium containing cells and/or tissue when desired, thereby enabling the device to be used continuously for at least one subsequent consecutive culturing/harvesting cycle. The portion of medium containing cells and/or tissue remaining from a previously harvested cycle may serve as inoculant for a next culture and harvest cycle.

57 Claims, 10 Drawing Sheets

U.S. PATENT DOCUMENTS

| | | |
|---|---|---|
| 4,491,549 A | 1/1985 | Fischer et al. |
| 4,668,632 A | 5/1987 | Young et al. |
| 4,708,938 A | 11/1987 | Hickinbotham |
| 4,713,345 A | 12/1987 | Ramsden |
| 4,717,668 A | 1/1988 | Keilman et al. |
| 4,725,548 A | 2/1988 | Karrer |
| 4,888,294 A | 12/1989 | Van Wezel et al. |
| 4,908,315 A * | 3/1990 | Kertz |
| 4,931,401 A | 6/1990 | Safi |
| 5,073,491 A | 12/1991 | Familletti |
| 5,081,036 A | 1/1992 | Familletti |
| 5,100,801 A | 3/1992 | Ward, Jr. et al. |
| 5,166,072 A | 11/1992 | Krauling et al. |
| 5,188,946 A | 2/1993 | Ward, Jr. et al. |
| 5,225,346 A | 7/1993 | Matsumiya et al. |
| 5,240,598 A | 8/1993 | Portier et al. |
| 5,246,855 A | 9/1993 | Katinger et al. |
| 5,267,791 A | 12/1993 | Christian et al. |
| 5,342,781 A | 8/1994 | Su |
| 5,372,945 A | 12/1994 | Alchas et al. |
| 5,409,833 A | 4/1995 | Hu et al. |
| 5,612,188 A | 3/1997 | Shuler et al. |

* cited by examiner

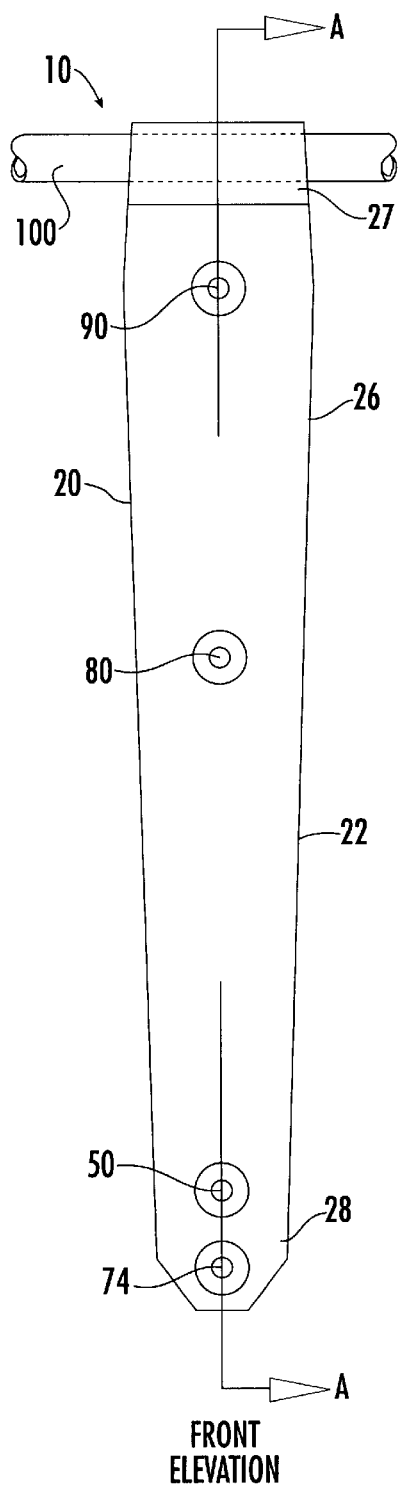
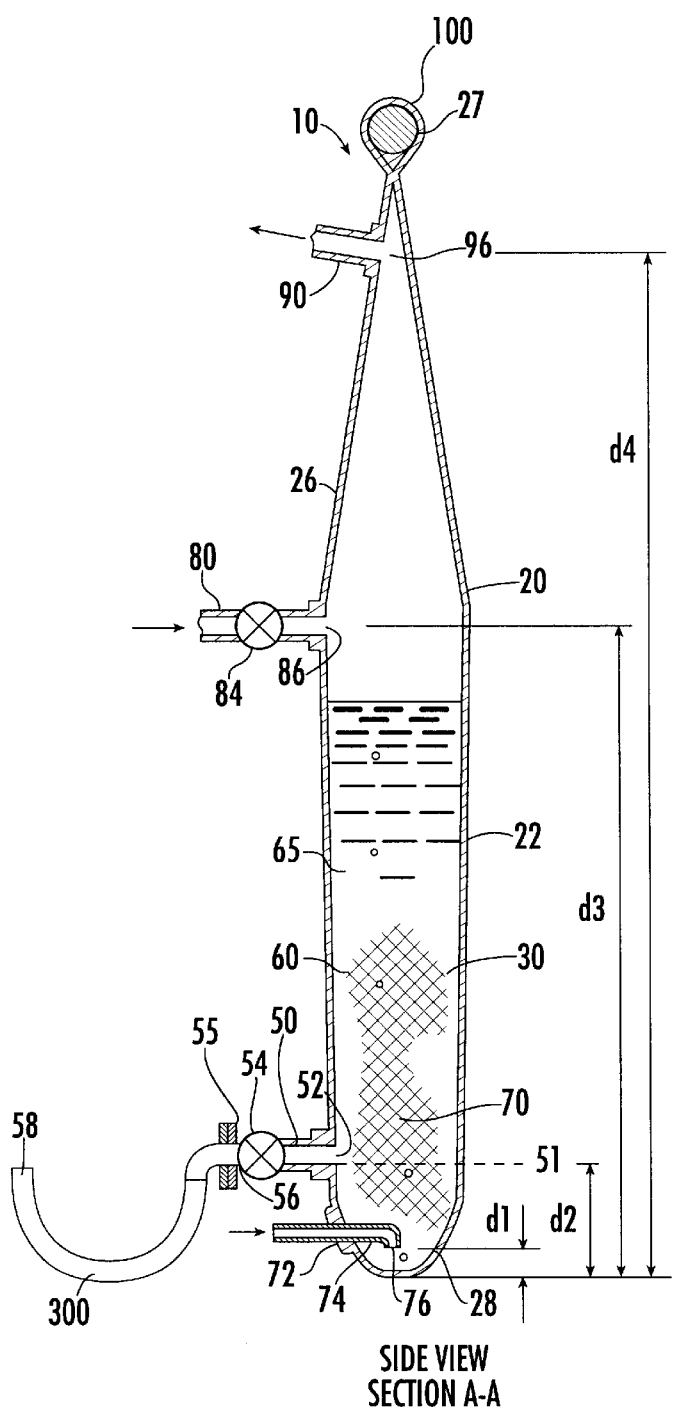
FIG. 1a.
FIG. 1b.

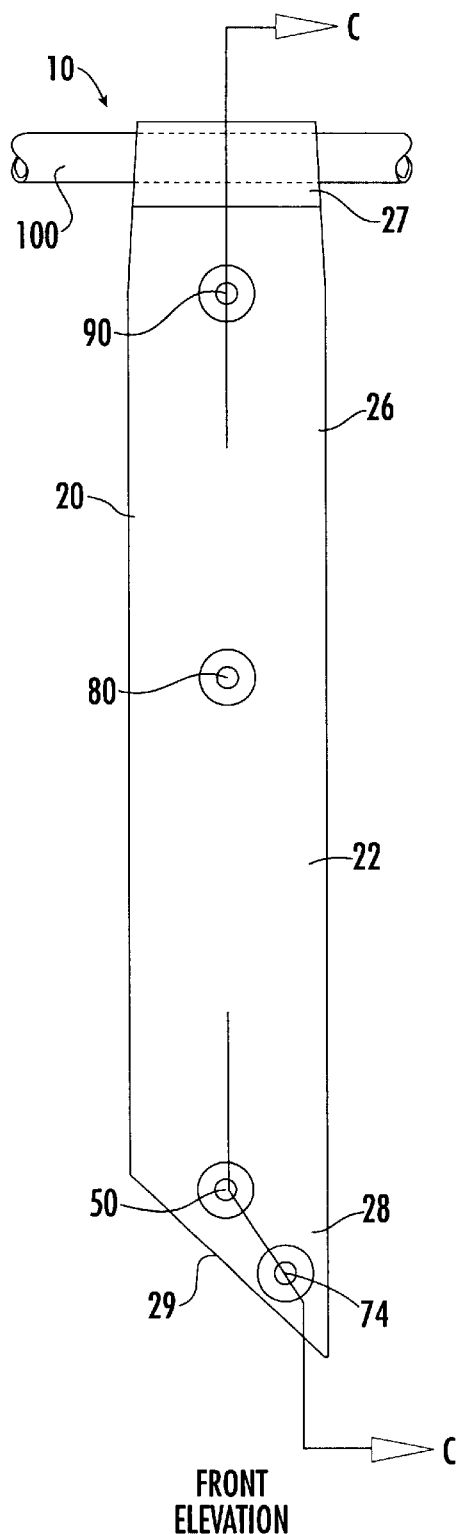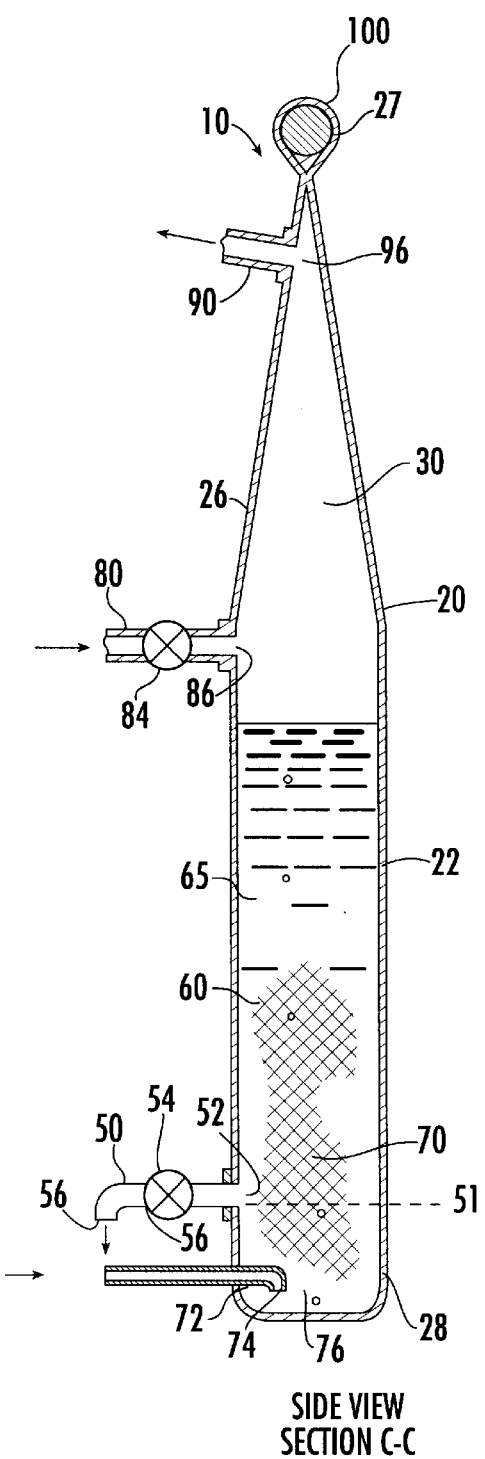
FIG. 2a.
FRONT ELEVATION
FIG. 2b.
SIDE VIEW
SECTION C-C

A-A

CELL/TISSUE CULTURING DEVICE AND METHOD

This application is a continuation in part (CIP) of PCT/IL97/00316 filed Sep. 26, 1997.

FIELD OF THE INVENTION

The present invention relates to devices for axenically culturing and harvesting cells and/or tissues, including bioreactors and fermentors. In particular this invention relates to such devices which are disposable but which nevertheless may be used continuously for a plurality of consecutive culturing/harvesting cycles prior to disposal of same. This invention also relates to batteries of such devices which may be used for large-scale production of cells and tissues.

BACKGROUND

Cell and tissue culture techniques have been available for many years and are well known in the art. The prospect of using such culturing techniques economically is for the extraction of secondary metabolites, such as pharmaceutically active compounds, various substances to be used in cosmetics, hormones, enzymes, proteins, antigens, food additives and natural pesticides, from a harvest of the cultured cells or tissues. While potentially lucrative, this prospect has nevertheless not effectively crystallised with industrial scale bioreactors which use slow growing plant and animal cultures because of the high capital costs involved.

Prior art technology for the production of cell and/or tissue culture at industrial scale, to be used for the production of such materials, is based on glass bioreactors and stainless steel bioreactors, which are expensive capital items. Furthermore, these types of industrial bioreactors comprise complicated and expensive mixing technologies such as impellers powered through expensive and complicated sterile seals; some expensive fermentors comprise an airlift multipart construction. Successful operation of these bioreactors often require the implementation of aeration technologies which constantly need to be improved. In addition, such bioreactors are sized according to the peak volume capacity that is required at the time. Thus, problems arise when scaling up from pilot plant fermentors to large scale fermentors, or when the need arises to increase production beyond the capacity of existing bioreactors. The alternative to a large-capacity bioreactor, namely to provide a number of smaller glass or stainless steel bioreactors whose total volume capacity matches requirements, while offering a degree of flexibility for increasing or reducing overall capacity, is nevertheless much more expensive than the provision of a single larger bioreactor. Furthermore, running costs associated with most glass and stainless steel bioreactors are also high, due to low yields coupled to the need for sterilising the bioreactors after every culturing cycle. Consequently, the products extracted from cells or tissues grown in such bioreactors are expensive, and cannot at present compete commercially with comparable products produced with alternative techniques. In fact, only one Japanese company is known to use the aforementioned cell/tissue culture technique commercially, using stainless steel bioreactors. This company produces Shikonin, a compound which is used almost exclusively in Japan. Industrial scale, and even large scale, bioreactor devices are traditionally permanent or semi-permanent components, and no disclosure nor suggestion of the concept of a disposable bioreactor device for solving the aforementioned problems regarding large scale cell/tissue culture production is known of. On the contrary, disposable fermentors and bioreactor devices are well known and exclusively directed to very small scale production volumes, such as in home brewing and for laboratory work. These bioreactor devices generally comprise a disposable bag which is typically cut open in order to harvest the cell/tissue yield, thus destroying any further usefulness of the bag. One such known disposable bioreactor is produced by Osmotec, Israel, (Agritech Israel, issue No. 11, Fall 1997, page 19) for small-scale use such as in laboratory research. This bioreactor comprises a conical bag having an inlet through which culture medium, air, inoculant and other optional additives may be introduced, and has a volume of only about 1.5 liters. Aeration is performed by introducing very small air bubbles which in many cases results in damage to cells, particularly in the case of plant cell cultures. In particular, these bags are specifically designed for a single culture/harvest cycle only, and the bag contents are removed by cutting off the bottom of the bag. These bags are therefore not directed towards an economical solution to the question of providing industrial quantities of the materials to be extracted from the culture, as discussed above.

The term "disposable" in the present application means that the devices (bags, bioreactors etc.) are designed to be thrown away after use with only negligible loss. Thus devices made from stainless steel, glass and even some types of rigid plastics are necessarily expensive devices and do not constitute a negligible loss for the operator of such devices. On the other hand, devices made from flexible cheap plastics, for example, are relatively inexpensive and may therefore be, and are, disposed of after use with negligible economic loss. Thus, the disposability of these bioreactor devices does not generally present an economic disadvantage to the user, since even the low capital costs of these items is offset against ease of use, storage and other practical considerations. In fact, at the low production levels that these devices are directed, such is the economy of the devices that there is no motivation to increase the complexity of the device or its operation for the sake of enabling such a device to be used continuously for more than one culturing/harvesting cycle.

Further, sterile conditions outside the disposable bioreactor devices are neither needed nor possible in many cases, and thus once opened to extract the harvestable yield, it is neither cost-effective, practical nor often possible to maintain the opening sterile, leading to contamination of the bag and whatever contents may remain inside. Thus, these disposable devices have no further use after one culturing cycle.

Disposable bioreactor devices are thus relatively inexpensive for the quantities and production volumes which are typically required by non-industrial-scale users, and are relatively easy to use by non-professional personnel. In fact it is this aspect of simplicity of use and low economic cost, which is related to the low production volumes of the disposable devices, that is a major attraction of disposable bioreactor devices. Thus, the prior art disposable bioreactor devices have very little in common with industrial scale bioreactors—structurally, operationally or in the economics of scale—and in fact teach away from providing a solution to the problems associated with industrial scale bioreactors, rather than in any way disclose or suggest such a solution.

The present invention therefore represents a revolutionary solution to the aforementioned problems, providing a disposable bioreactor device for the large scale production of cell/tissue cultures. The device of the present invention, while essentially disposable, is characterised in comprising a reusable harvesting outlet for enabling harvesting of at least a portion of the medium containing cells and/or tissue when desired, thereby enabling the device to be used continuously for one or more subsequent consecutive culturing/harvesting cycles. In an industrial environment, sterility of the harvesting outlet during and after harvesting may be assured to a significantly high degree at relatively low cost, by providing, for example, a sterile hood in which all the necessary connections and disconnections of services to and from the device may be performed. When eventually the device does become contaminated it may then be disposed of with relatively little economic loss. Such devices may be cheaply manufactured, even for production volumes of 50 liters or more of culture. Further, the ability to perform a number of culturing/harvesting cycles is economically lucrative, lowering even further the effective cost per device. A battery of such devices can be economically arranged, and the number of devices in the battery may be controlled to closely match production to demand. Thus, the transition from pilot plant bioreactors to large scale production may also be achieved in a relatively simple and economic manner by adding more devices to the battery. Further, the relatively low production volume of each device, coupled with the lack of solid mixers, results in relatively higher yields as compared to typical stainless steel bioreactors.

An aim of the present invention is to provide a device, and associated method, for axenically culturing and harvesting cells and/or tissue, and which does not have the aforegoing disadvantages.

Another aim of the present invention is to provide such a device which is economical to produce and simple to use.

Another aim of the present invention is to provide such a device which is disposable, but nevertheless may be used continuously for a plurality of consecutive cycles of culturing and harvesting desired cells and/or tissues.

Another aim of the present invention is to provide such a device wherein inoculant is only required to be provided for the first culturing cycle, while inoculant for subsequent cycles is provided by a portion of the culture broth which remains in the device after harvesting same in a preceding cycle.

Another aim of the present invention is to provide a battery of such devices for industrial scale production of cells and/or tissues.

SUMMARY OF THE INVENTION

A disposable device, and corresponding method, for axenically culturing and harvesting cells and/or tissue in at least one cycle, said device comprising a sterilisable transparent and/or translucent disposable container having a top end and a bottom end, which container may be at least partially filled with a suitable sterile biological cell and/or tissue culture medium and/or axenic inoculant and/or sterile air and/or required other sterile additives, said container comprising:—gas outlet means for removing excess air and/or waste gases from said container; additive inlet means for introducing said inoculant and/or said culture medium and/or said additives into said container; and characterised in further comprising reusable harvesting means comprising suitable flow control means for enabling harvesting of at least a desired portion of the said medium containing cells and/or tissue when desired, thereby enabling said device to be used continuously for at least one further consecutive culturing/harvesting cycle, wherein a remainder of said medium containing cells and/or tissue, remaining from a previously harvested cycle may serve as inoculant for a next culture and harvest cycle, wherein said culture medium and/or said required additives are provided. The said device may further comprise air inlet means for introducing sterile air in the form of bubbles into said culture medium through an inlet opening. Medium and air and any other required additives are provided in suitable quantities during each cycle to enable culture of said cells and/or tissue from said inoculant. The said device may be disposed of when contaminated. In a second aspect of the invention, a battery of these devices, suitably interconnected, enables the scale of production of cells/tissues to be adjusted as required.

DESCRIPTION OF THE FIGURES

FIGS. 1a and 1b illustrate the main components of a first embodiment of the device of the present invention in front elevation and in cross-sectional side view, respectively.

FIGS. 2a and 2b illustrate the main components of a second embodiment of the device of the present invention in front elevation and in cross-sectional side view, respectively.

DESCRIPTION

The present invention relates to a disposable device for axenically culturing and harvesting cells and/or tissue in at least one cycle, said device comprising a sterilisable transparent and/or translucent disposable container having a top end and a bottom end, which container may be at least partially filled with a suitable sterile biological cell and/or tissue culture medium and/or axenic inoculant and/or sterile air and/or required other sterile additives, said container comprising:

(i) gas outlet means for removing excess air and/or waste gases from said container;

(ii) additive inlet means for introducing said inoculant and/or said culture medium and/or said additives into said container;

and characterised in further comprising (iii) reusable harvesting means comprising suitable flow control means for enabling harvesting of at least a desired portion of the said medium containing cells and/or tissues when desired, thereby enabling said device to be used continuously for at least one further consecutive culturing/harvesting cycle, wherein a remainder of said medium containing cells and/or tissue, remaining from a previous harvested cycle, may serve as inoculant for a next culture and harvest cycle, wherein said culture medium and/or said required additives are provided.

The present invention further relates to such a device further comprising air inlet means for introducing sterile air in the form of bubbles into said culture medium through a first inlet opening, said air inlet means being connectable to a suitable air supply.

Figure 3:
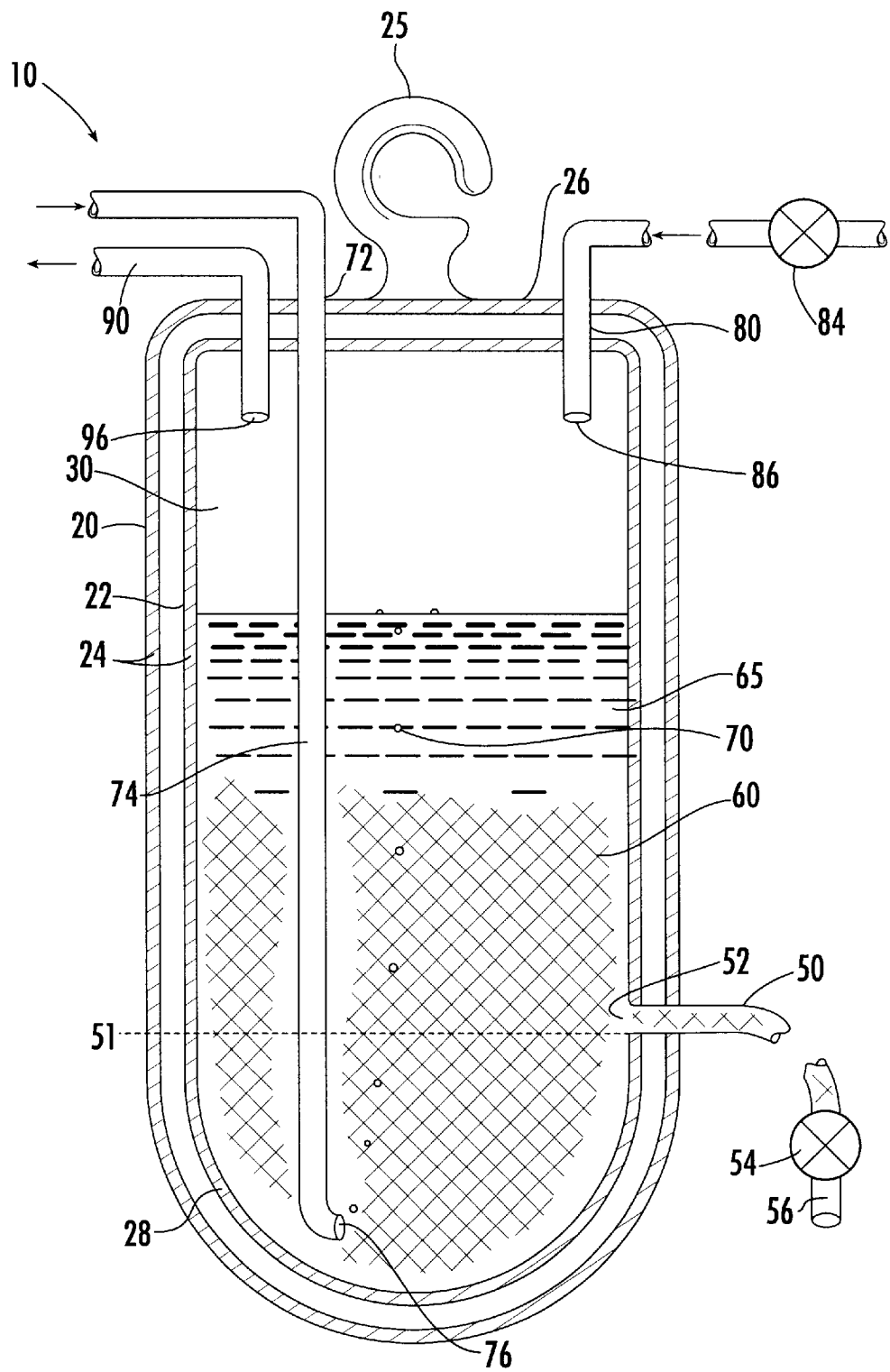
FIG. 3 illustrates the main components of a third embodiment of the device of the present invention in cross-sectional side view.

Thus, with reference to FIGS. 1, 2, and 3, corresponding respectively to a first, second and third embodiments of the device, the device, generally designated (10), comprises a transparent and/or translucent container (20), having a top end (26) and a bottom end (28). The said container (20) comprises a side wall (22) which is preferably substantially cylindrical, though other shapes such as rectangular or polyhedral, for example, may also be suitable. Preferably, the said bottom end (28) is suitably shaped to minimise sedimentation thereat. For example, in the first embodiment, the said bottom end (28) is substantially frustro-conical or at least comprises upwardly sloping walls. In the second embodiment, the bottom end (28) comprises one upwardly sloping wall (29). In the third embodiment, the bottom end (28) is substantially cylindrical or alternatively convex. The aforementioned configurations of the bottom end (28), in conjunction with the location of the outlet (76) (hereinafter described) near the bottom end (28), enables air supplied via said outlet (76) to induce a mixing motion to the container contents at the bottom end (28) which effectively minimises sedimentation thereat. Nevertheless, the bottom end may be substantially flat in other embodiments of the present invention. The container (20) comprises an internal fillable volume (30) which is typically between 5 and 50 liters, though said device (10) may alternatively have an internal volume greater than 50 liters or less than 5 liters. Said internal volume (30) may be filled with a suitable sterile biological cell and/or tissue culture medium (65) and/or axenic inoculant (60) and/or sterile air and/or required other sterile additives such as antibiotics or fungicides for example, as hereinafter described. In the aforementioned embodiments, the container (20) is substantially non-rigid, being made preferably from a non-rigid plastics material chosen from the group comprising polyethylene, polycarbonate, a copolymer of polyethylene and nylon, PVC and EVA, for example. Optionally, the container (20) may be made from a laminate of more than one layer of said materials.

As shown for the third embodiment in FIG. 3, the said container (20) may optionally comprise two concentric outer walls (24) to enhance mechanical strength and to minimise risk of contamination of the contents via the container walls.

In the first, second and third embodiments, said device (10) is for aerobic use. Thus the container (20) further comprises at least one air inlet means for introducing sterile air in the form of bubbles (70) into said culture medium (65) through at least one air inlet opening (72). In the aforementioned embodiments, said air inlet means comprises at least one pipe (74) connectable to a suitable air supply (not shown) and extending from said inlet opening (72) to a location inside said container (20) at a distance d1 from the bottom of said bottom end (28), wherein d1 may be typically around 1 cm, though it could be greater or smaller than 1 cm. The said pipe (74) may be made from silicon or other suitable plastic material and is preferably flexible. The pipe (74) thus comprises an air outlet (76) of suitable diameter to produce air bubbles (70) of a required mean diameter. These bubbles not only aerate the medium (65), but also serve to mix the contents of the container, thereby minimising sedimentation at the bottom end (28) as well, as hereinbefore described. The size of the bubbles delivered by the air inlet means will vary according to the use of the device, ranging from well under 1 mm to over 10 mm in diameter. In some cases, particularly relating to plant cells, small bubbles may actually damage the cell walls, and a mean bubble diameter of not less than 4 mm substantially overcomes this potential problem. In other cases, much smaller bubbles are beneficial, and a sparger may be used at the air outlet (76) to reduce the size of the bubbles. In yet other cases air bubbles of diameter 10 mm or even greater may be optimal. Optionally, said outlet (76) may be restrained in position at said bottom end (28) by means of a tether (not shown) or other means known in the art.

In other embodiments, said device (10) is for anaerobic use, and thus does not comprise the said air inlet means.

In a fourth and fifth embodiments of the present invention, and with reference to FIGS. 5 and 6 respectively, the device (10) also comprises a transparent and/or translucent container (20), having a top end (26) and a bottom end (28). The said container (20) comprises a side wall (22) which is preferably substantially rectangular in cross-section, having a large length to width aspect ratio, as shown for the fourth embodiment of the present invention (FIG. 5). Thus, the container (20) of the fourth embodiment is substantially box-like, having typical height-length-width dimensions of 130 cm×70 cm×10 cm, respectively. The height to length ratio of the device is typically between, for example, about 1 and about 3, and preferably about 1.85. The height-to-width ratio of the device is typically between 5 and about 30, and preferably about 13. Alternatively, and as shown in FIG. 6 with respect to the fifth embodiment of the present invention, the sidewall (22) may comprise a substantially accordion-shaped horizontal cross-section, having a series of parallel crests (221) intercalated with troughs (222) along the length of the container (20), thereby defining a series of adjacent chambers (223) in fluid communication with each other. Optionally, the said sidewall (22) of the fifth embodiment may further comprise a plurality of vertical webs (224), each internally joining pairs of opposed troughs, thereby separating at least a vertical portion of each said chamber (223) from adjacent chambers (223). The webs (224) not only provide increased structural integrity to the container (20), but also effectively separates the container (20) into smaller volumes, providing the advantage of enhanced circulation. In other words, the effectiveness of air bubbles in promoting cell circulation is far higher in smaller enclosed volumes than in a larger equivalent volume. In fact, a proportionately higher volume flow rate for the air bubbles is required for promoting air circulation in a large volume than in a number of smaller volumes having the same combined volume of medium. In the fourth and fifth embodiments, said bottom end (28) is substantially semi-cylindrical or may be alternatively convex, substantially flat, or any other suitable shape. In the fourth and fifth embodiments, the container (20) comprises an internal fillable volume (30) which is typically between 10 and 100 liters, though said device (10) may alternatively have an internal volume greater than 100 liters, and also greater than 200 liters. Said internal volume (30) may be filled with a suitable sterile biological cell and/or tissue culture medium (65) and/or axenic inoculant (60) and/or sterile air and/or required other sterile additives such as antibiotics or fungicides for example, as hereinafter described. In the aforementioned fourth and fifth embodiments, the container (20) is substantially non-rigid, being made preferably from a non-rigid plastics material chosen from the group comprising polyethylene, polycarbonate, a copolymer of polyethylene and nylon, PVC and EVA, for example, and, optionally, the container (20) may be made from a laminate of more than one layer of said materials.

As for the first, second and third embodiments, said device (10) of the fourth and fifth embodiments is also for aerobic use. In the fourth and fifth embodiments, the container (20) further comprises at least one air inlet means for introducing sterile air in the form of bubbles (70) into said culture medium (65) through a plurality of air inlet openings (72). In the fourth and fifth embodiments, said air inlet means comprises at least one air inlet pipe (74) connectable to a suitable air supply (not shown) and in communication with a plurality of secondary inlet pipes (741), each secondary inlet pipe (741) extending from said inlet opening (72) to a location inside said container (20) at a distance d1 from the bottom of said bottom end (28), wherein d1 may be typically around 1 cm, though it could be greater or smaller than 1 cm. The plurality of inlet openings (72), are horizontally spaced one from another by a suitable spacing d5, typically between about 5 cm and about 25 cm, and preferably about 10 cm. The said at least one air inlet pipe (74) and secondary inlet pipes (741) may be made from silicon or other suitable plastic material and is preferably flexible. Each of said secondary inlet pipes (741) thus comprises an air outlet (76) of suitable diameter to produce air bubbles (70) of a required mean diameter. These bubbles not only aerate the medium (65), but also serve to mix the contents of the container, thereby minimising sedimentation at the bottom end (28) as well, as hereinbefore described. The size of the bubbles delivered by the air inlet means will vary according to the use of the device, ranging from well under 1 mm to over 10 mm in diameter. In some cases, particularly relating to plant cells, small bubbles may actually damage the cell walls, and a mean bubble diameter of not less than 4 mm substantially overcomes this potential problem. In other cases, much smaller bubbles are beneficial, and a sparger may be used at least one of said air outlets (76) to reduce the size of the bubbles. In yet other cases air bubbles of diameter 10 mm or even greater may be optimal. Optionally, each said outlet (76) may be restrained in position at said bottom end (28) by means of a tether (not shown) or other means known in the art.

The fourth and fifth embodiments of the present invention are especially adapted for processing relatively large volumes of inoculant.

In all the aforementioned embodiments, the said air inlet means optionally comprises a suitable pressure gauge for monitoring the air pressure in the container (20). Preferably, said pressure gauge is operatively connected to, or alternatively comprises, a suitable shut-off valve which may be preset to shut off the supply of air to the container (20) if the pressure therein exceeds a predetermined value. Such a system is useful in case of a blockage in the outflow of waste gases, for example, which could otherwise lead to a buildup of pressure inside the container (20), eventually bursting the same.

The said container (20) further comprises at least one gas outlet means for removing excess air and/or waste gases from said container (20). These gases collect at the said top end (26) of the said container (20). The said gas outlet means may comprise a pipe (90) having an inlet (96) at or near the said top end (26), at a distance d4 from the bottom of the said bottom end (28), wherein d4 is typically 90 cm for the first, second and third embodiments, for example. The said pipe (90) may be made from silicon or other suitable plastic material and is preferably flexible. Said pipe (90) is connectable to a suitable exhaust means (not shown) by known means. The said exhaust means further comprises means, such as a suitable one-way valve or filter (typically a 0.2 μm filter), for example, for substantially preventing introduction of contaminants into said container via said gas outlet means. At least a portion of the top end (26) may be suitably configured to facilitate the collection of waste gases prior to being removed via said inlet (96). Thus, in the first and second embodiments, the upper portion of the top end (26) progressively narrows to a minimum cross sectional area near the location of the inlet (96). Alternatively, at least the upper portion of the top end (26) may be correspondingly substantially frustro-conical or convex. In the fourth and fifth embodiments, the said top end (26) may be convex, or relatively flat, for example, and the inlet (96) may be conveniently located at or near a horizontal end of the top end (26).

The said container (20) further comprises additive inlet means for introducing said inoculant and/or said culture medium and/or said additives into said container. In the aforementioned embodiments, said additive inlet means comprises a suitable pipe (80) having an outlet (86) preferably at or near the said top end (26), at a distance d3 from the bottom of the said bottom end (28), wherein d3 for the first embodiment is typically approximately 68 cm, for example. The said pipe (80) may be made from silicon or other suitable plastic material and is preferably flexible. Said pipe (80) is connectable by known means to a suitable sterilised supply of said inoculant and/or said culture medium and/or said additives. Said additive inlet means further comprises means for substantially preventing introduction of contaminants into said container via said additive inlet means, and comprises, in these embodiments, a suitable one-way valve or filter (84). Typically, the level of contents of the container (20) remains below the level of the said outlet (86).

The said container (20) further comprises reusable harvesting means for harvesting at least a desired first portion of the said medium containing cells and/or tissue when desired, thereby enabling said device to be used continuously for at least one subsequent culturing cycle. A remaining second portion of said medium containing cells and/or tissue serves as inoculant for a next culture and harvest cycle, wherein said culture medium and/or said required additives provided. Said harvesting means may also be used to introduce the original volume of inoculant into the container, as well as for enabling the harvested material to flow therethrough and out of the container. In the aforementioned embodiments, said harvesting means comprises a pipe (50) having an inlet (52) in communication with said internal volume (30), and an outlet (56) outside said container (20). The said pipe (50) may be made from silicon or other suitable plastic material and is preferably flexible. Said pipe (50) is of a relatively large diameter, typically about 2 cm, since the harvested cell and/or tissue flow therethrough may contain clumps of cell particles that may clog narrower pipes. Preferably, said inlet (52) is located near the bottom end (28) of the said container (20), so that only the container contents above said inlet (52) are harvested. Thus, at the end of each harvesting cycle, said second portion of medium containing cells and/or tissues automatically remains at the said bottom end (28) of the said container (20), up to a level below the level (51) of the said inlet (52), which is at a distance d2 from the bottom of said bottom end (28). Typically, d2 is about 25 cm for the first embodiment. Alternatively, said inlet (52) may be located at the lowest point in the said container (20), wherein the operator would manually ensure that a suitable portion of medium containing cells and/or tissue would remain in the container (20) after harvesting a desired portion of medium and cells and/or tissue. Said harvest means further comprises flow control means such as a suitable valve (54) and/or an aseptic connector (55) for closing off and for permitting the flow of material into or out of said container (20) via said harvest means. Typically, said aseptic connector (55) is made from stainless steel, and many examples thereof are known in the art. Preferably, the said harvest means further comprise contamination prevention means for substantially preventing introduction of contaminants into said container via said harvesting means after harvesting. In the first, second, third, fourth and fifth embodiments, said contamination prevention means comprises a fluid trap (300). Said fluid trap (300) is preferably in the form of a substantially U-shaped hollow tube, one arm of which is mounted to the outlet (56) of the said harvesting means, and the other arm having an external opening (58), as shown for the first embodiment, for example, in FIG. 1(b). Harvested cells/tissue may flow out of the device (10) via said harvesting means, fluid trap (300) and said opening (58), to be collected thereafter in a suitable receiving tank as hereinafter described. After harvesting is terminated, air could possibly be introduced into the harvesting means via opening (56), accompanied by some back-flow of harvested material, thereby potentially introducing contaminants into the device. The said U-tube (300) substantially overcomes this potential problem by trapping some harvested material, i.e., cells/tissues, downstream of the opening (56) thereby preventing air, and possible contaminants, from entering the harvesting means. Once the harvesting means is closed off via said valve (54), the U-tube (300) is removed and typically sterilised for the next use or discarded. The said U-tube (300) may be made from stainless steel or other suitable rigid plastic materials.

In the aforementioned embodiments, said remaining second portion of said medium containing cells and/or tissue typically comprises between 10% and 20% of the original volume of said culture medium and said inoculant, though said second portion may be greater than 20%, up to 45% or more, or less than 10%, down to 2.5% or less, of the said original volume, if required.

Said device (10) optionally further comprises attachment means for attaching same to an overhanging support structure. In the aforementioned embodiments, said support structure may comprise a bar (100) (FIGS. 1, 2, 5) or rings (not shown). In the third embodiment, said attachment means may comprise a hook (25) preferably integrally attached to the said top end (26) of the said container (20). Alternatively, and as shown for the first and second embodiments in FIGS. 1 and 2 respectively, said attachment means may comprise a preferably flexible and substantially cylindrical loop (27) of suitable material, typically the same material as is used for the container (20), either integral with or suitably attached (via fusion welding, for example) to the top end (26) of the device. Alternatively, and as shown for the fourth embodiment in FIG. 5, said attachment means may comprise a preferably flexible and substantially cylindrical aperture (227) made in the sidewall (22) of said container (20), extending through the depth thereof. The fifth embodiment may optionally be supported by a series of hooks (not shown) integrally or suitably attached preferably to the top end (26) of the device (10).

Optionally, the said containers may be supported in a suitable support jacket. For example, in the fourth embodiment, the said device (10) may be supported in a support jacket consisting of a suitable outer support structure comprising an internal volume sized and shaped to complement the datum external geometry of at least the sidewall (22) and bottom end (28) of the device when nominally inflated. The outer support structure may be substantially continuous, with openings to allow access to the inlets and outlets to the device (10), and further has a suitable door or opening either at the side, top or bottom to allow a device (10) to be inserted into the support jacket or removed therefrom. The datum geometry of the device may be defined as the shape of the device (10) when it is inflated to its design capacity. At this point, its shape is nominally is design shape, and therefore its internal volume is nominally its design volumetric capacity. However, when such a device comprising flexible walls is actually filled with a liquid medium, the geometry of the device tends to deviate from the datum geometry, tending to bulge preferentially at the bottom the device where the pressure is greatest, and increasing stresses in the wall material considerably. A support jacket as described for example and having the required structural attributes also helps in maintaining the geometry of the device, and reduces the wall stresses, minimising risk of rupture of the sidewall (22), for example and thereby ensuring a longer working life for each device.

Figure 9:
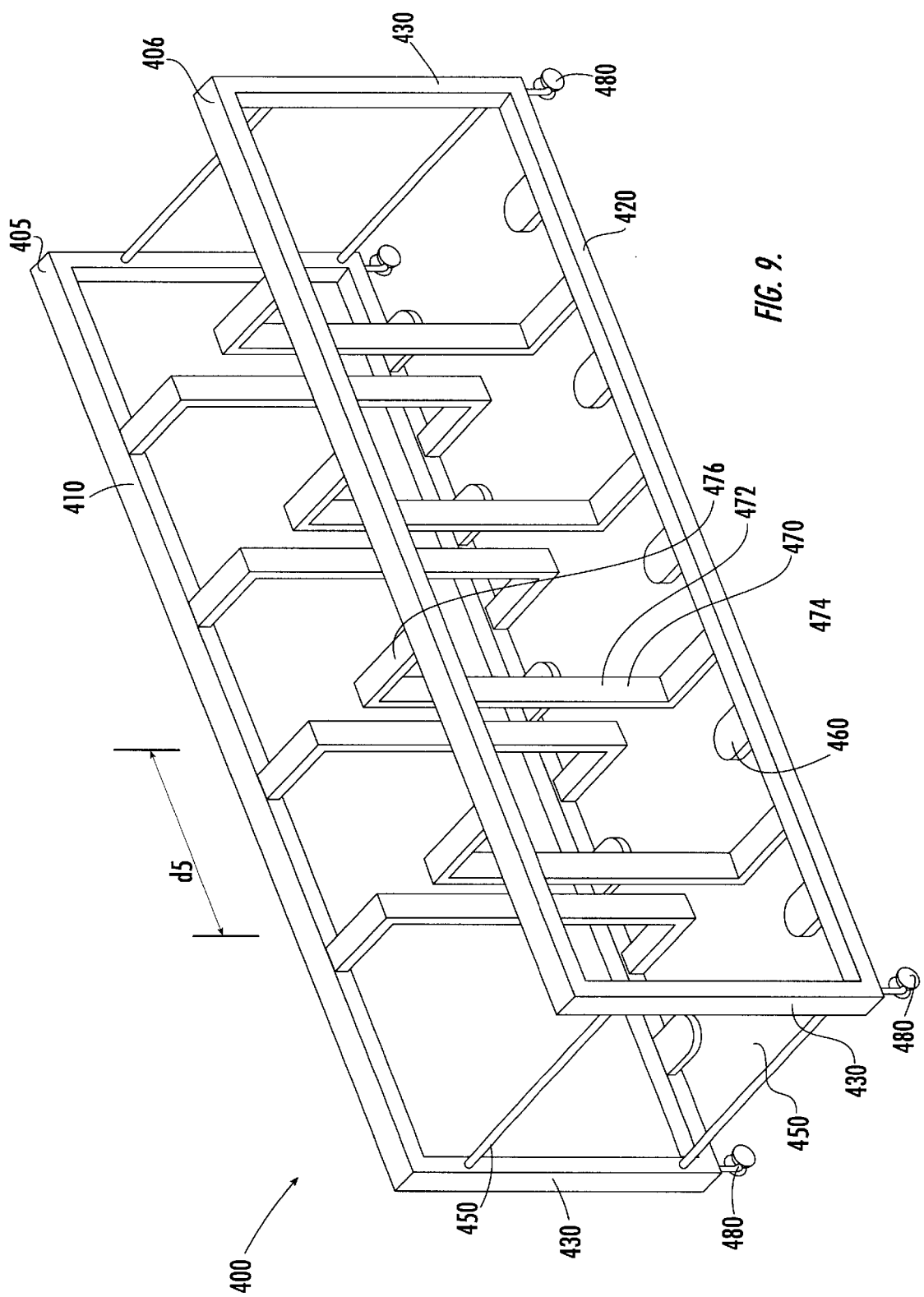
FIG. 9 illustrates a support structure for use with the embodiments of FIGS. 5 to 8.

Alternatively, the said containers may be supported in a suitable support structure. For example, in the fourth and fifth embodiments of the present invention, the said device (10) may be supported in a support structure (400) comprising a pair of opposed frames (405), (406), as illustrated, for example, in FIG. 9. Each frame (405), (406) is typically rectangular comprising substantially parallel and horizontal upper and lower load-carrying members (410) and (420) respectively, spaced by a plurality of substantially parallel vertical support members (430), at least at each longitudinal extremity of the load-carrying members (410), (420), and integrally or otherwise suitably joined to the said upper and lower load-carrying members, (410) and (420) respectively. The said lower support member (420) of each frame (405) and (406) comprises suitably shaped lower supports adapted for receiving and supporting a corresponding portion of the said bottom end (28) of the containers (20). Typically, the said lower supports may take the form of a suitably shaped platform projecting from each of the lower support members (420) in the direction of the opposed frame. Alternatively, the said lower supports may take the form of a plurality of suitably shaped tabs (460) projecting from each of the lower support members (420) in the direction of the opposed frame. The said frames (405), (406) are spaced from each other by strategically located spacing bars (450), such that the container (20) may be removed relatively easily from the support structure (400) and a new container (20) maneuvered into place, i.e., without the need to dismantle the support frame (400). The said spacing bars (450) may be integrally connected to the frames (405), (406), as by welding for example. Preferably, though, the spacing bars (450) are releasably connected to the frames (405), (406), such that the frames (405), (406) may be separated one from the other, and also permitting the use of different sized spacing bars to connect the frames (405), (406), thereby enabling the support structure (400) to be used with a range of containers (20) having different widths. Optionally, and preferably, the said frames (405), (406) each comprise at least one interpartitioning means (470). Said interpartitioning means (470) may take the form of a vertical web projecting from each frame (405), (406) in the direction of the opposed frame, and serves to push against the sidewall (22) at a predetermined position, such that opposed pairs of said interpartitioning means (470) effectively reduce the width of the container (20) at the predetermined position, thereby creating, between adjacent opposed pairs of interpartitioning means (470), for example, a partitioning or semi partitioning of the internal space (30) of the container (20). Thus, the interpartitioning means (470) may typically deform the sidewall (22) of a container (20) according to the fourth embodiment (see FIG. 5) to a shape resembling that of the sidewall (22) of the fifth embodiment (see FIG. 6). Of course, when used with a container (20) according to the fifth embodiment of the present invention, the said interpartitioning means (470) are located on the frames (405), (406) such as to engage with the said troughs (222) of the sidewall (22), and thus particularly usefull in maintaining the shape of the said containers (20). Thus, adjacent partitioning means (470) on each frame are spaced advantageously spaced a distance (d5) one from another. Preferably, said interpartitioning means (470) comprise suitable substantially vertical members (472) spaced from the said upper and lower support members, (410), (420), in a direction towards the opposed frame by means of suitable upper and lower struts (476), (474) respectively. The said support structure (400) thus not only provides structural support for the said containers (20), particularly of the fourth and fifth embodiments, it also provides many open spaces between each of the load carrying members for enabling each of the air inlet means, the gas outlet means, the harvesting means and the additive inlet means to pass therethrough. Optionally, said support structure (400) may comprise rollers or castors (480) for easing transportation of the said containers (20) within a factory environment, for example.

Figure 4:
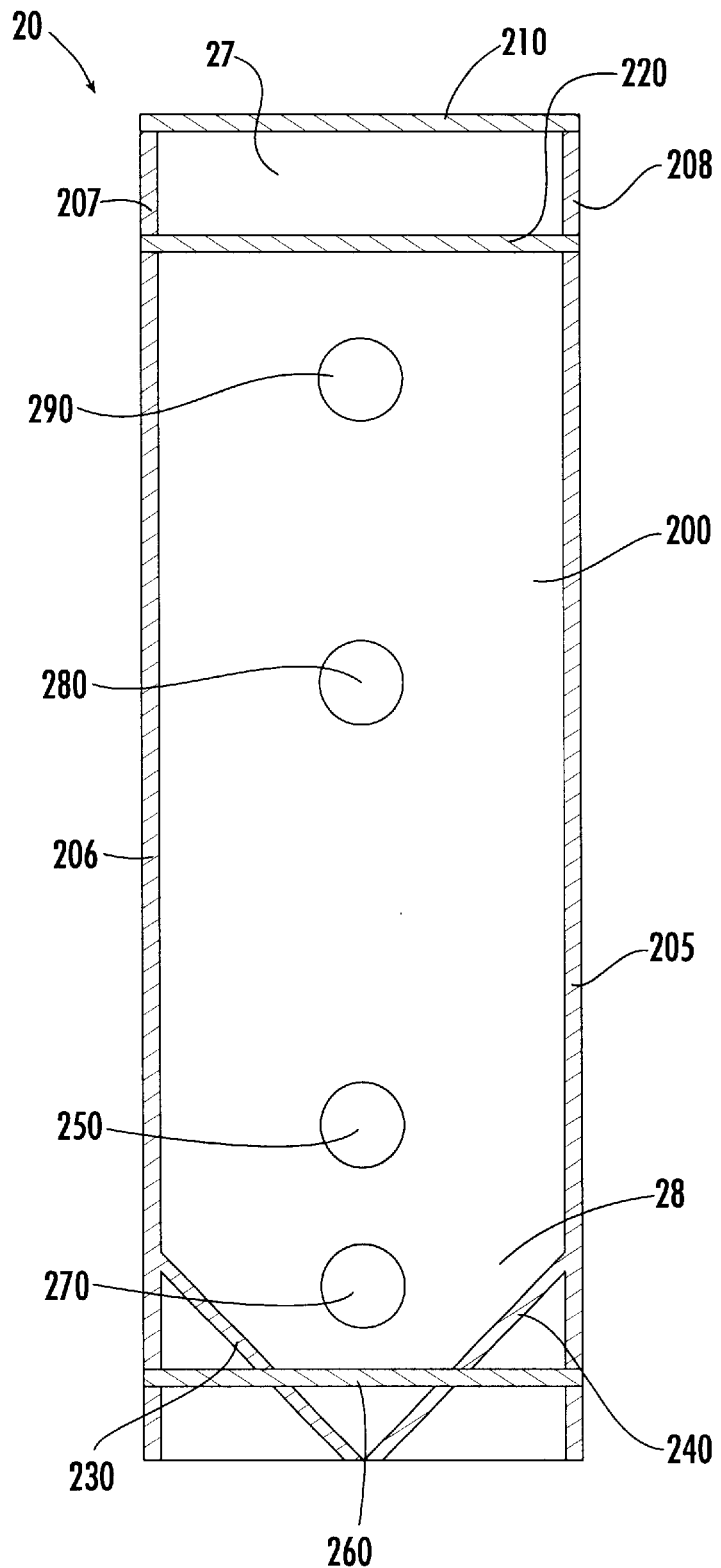
FIG. 4 illustrates the seam lines of the first embodiment of the device of the present invention in front elevation.
Figure 5A:
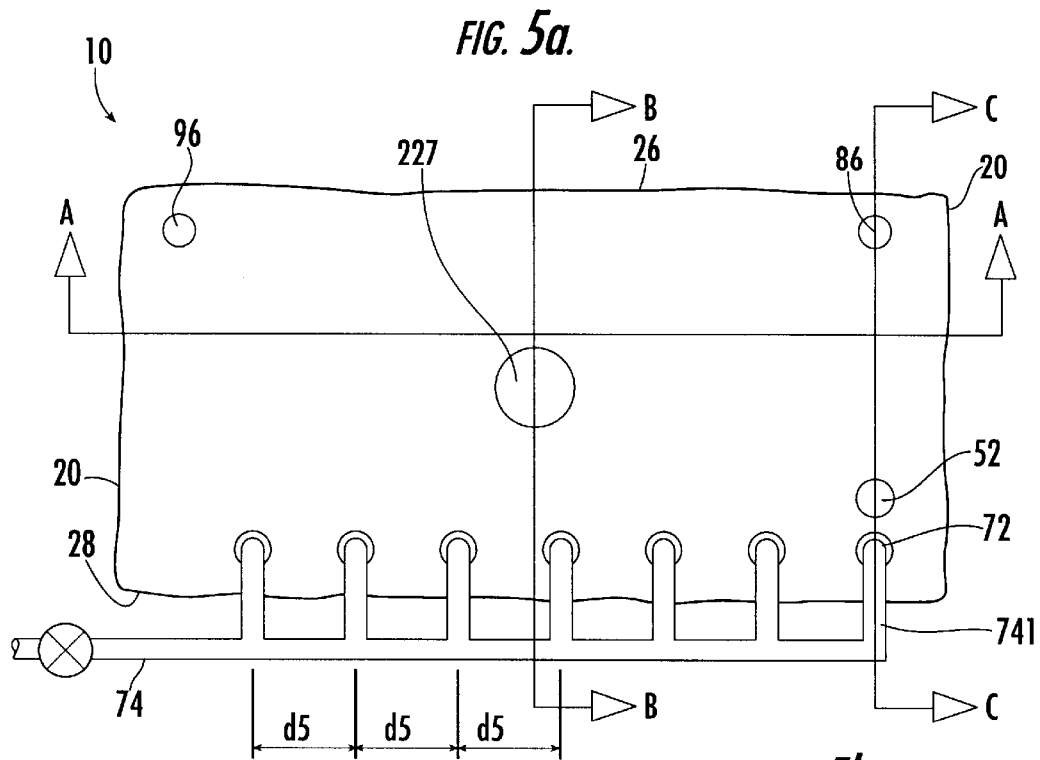
FIGS. 5a and 5b illustrate the main components of a fourth embodiment of the device of the present invention in side view and in cross-sectional top view, respectively.
Figure 5B:
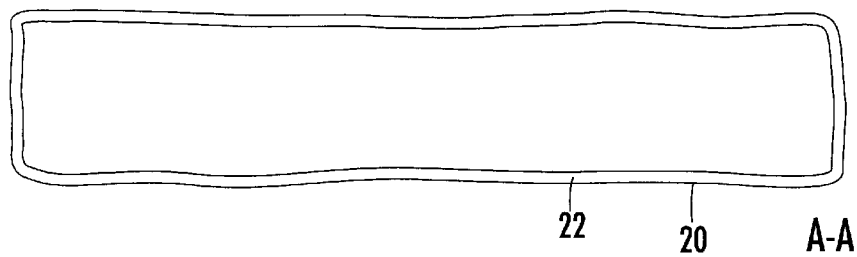
Figure 5C:
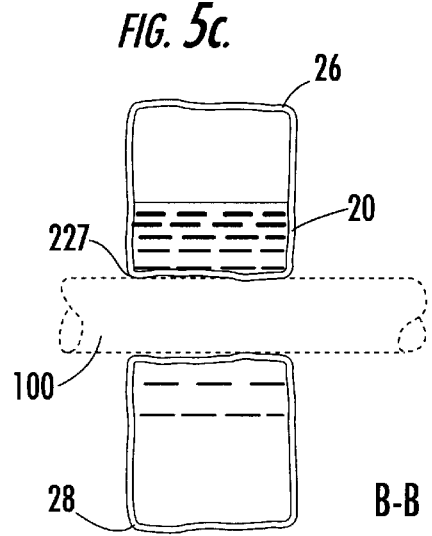
FIGS. 5(c) and 5(d) illustrate transverse cross-sections of the fourth embodiment taken along lines B—B and C—C in FIG. 5(a).
Figure 5D:
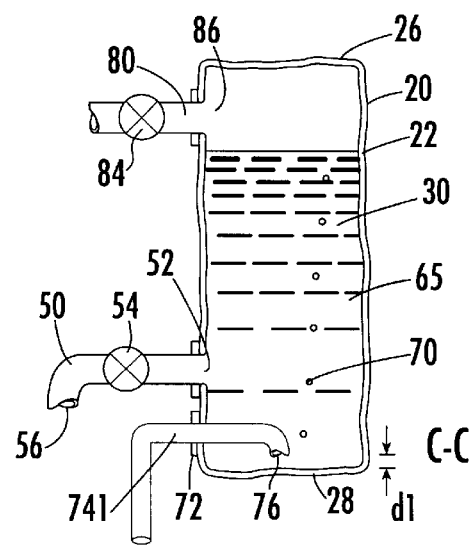
Figure 6A:
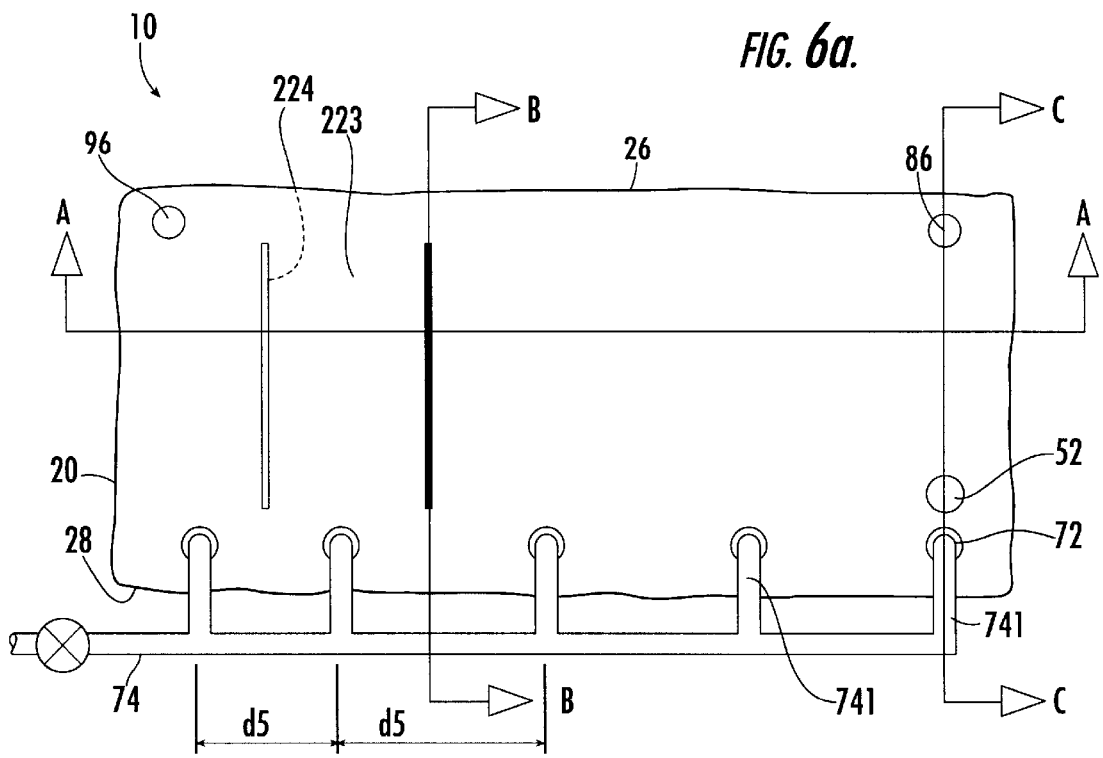
FIGS. 6a and 6b illustrate the main components of a fifth embodiment of the device of the present invention in side view and in cross-sectional top view, respectively.
Figure 6B:
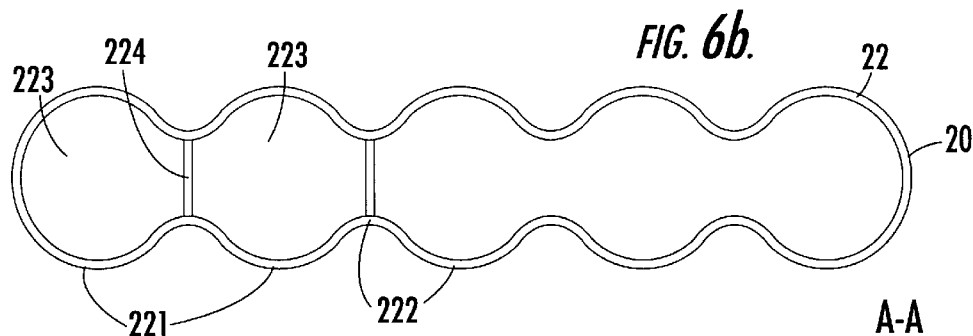
Figure 6C:
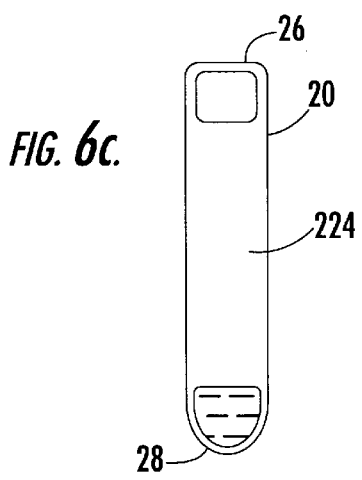
FIGS. 6(c) and 6(d) illustrate transverse cross-sections of the fifth embodiment taken along lines B—B and C—C in FIG. 6(a).
Figure 6D:
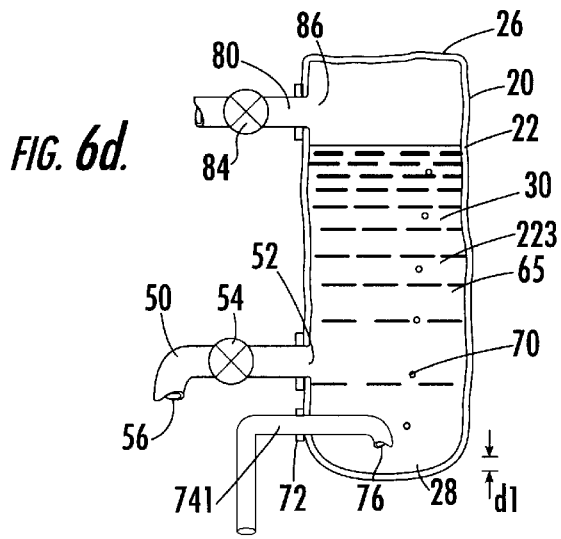
Figure 7:
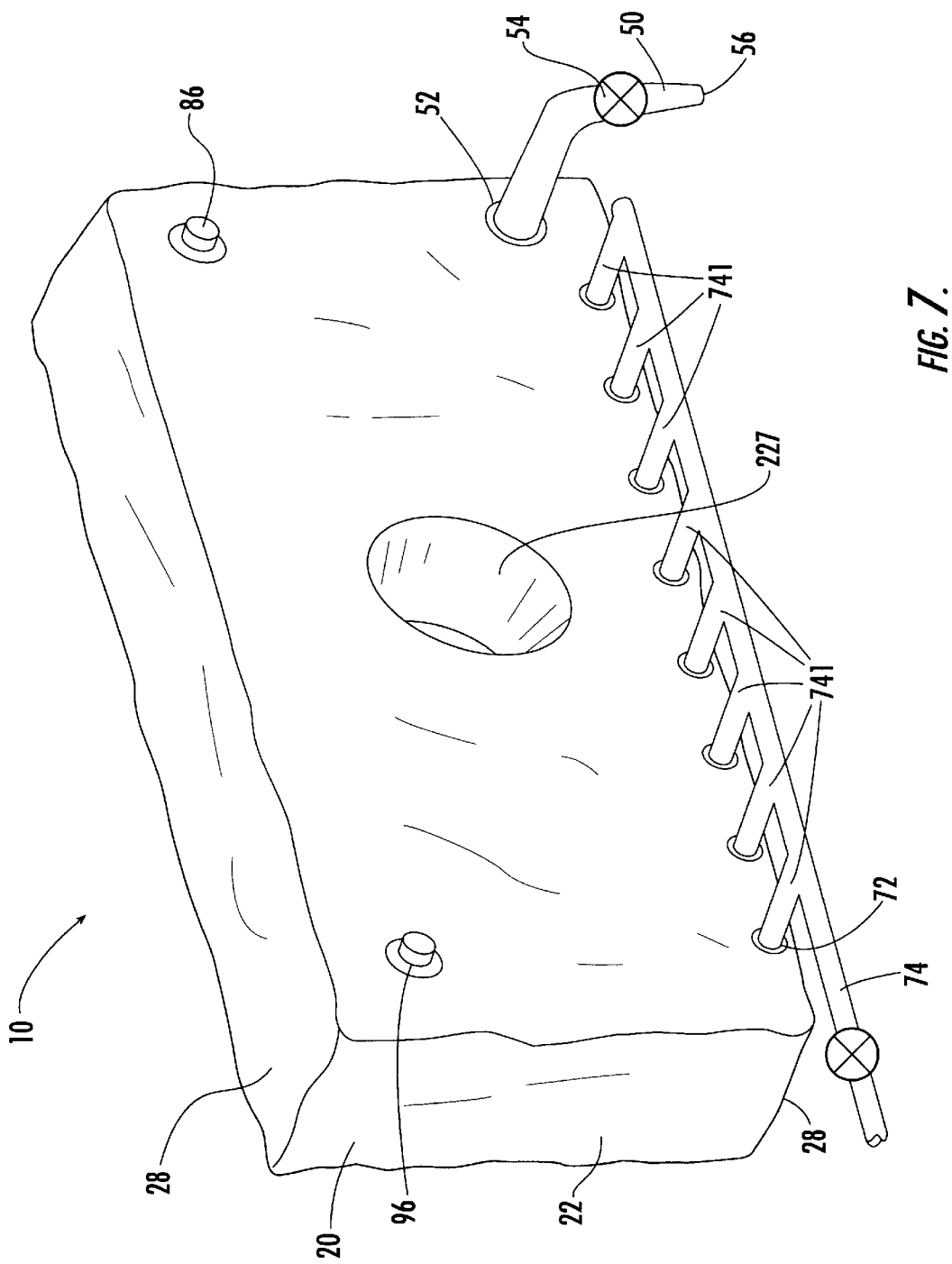
FIG. 7 illustrates the embodiment of FIG. 5 in perspective view.
Figure 8:
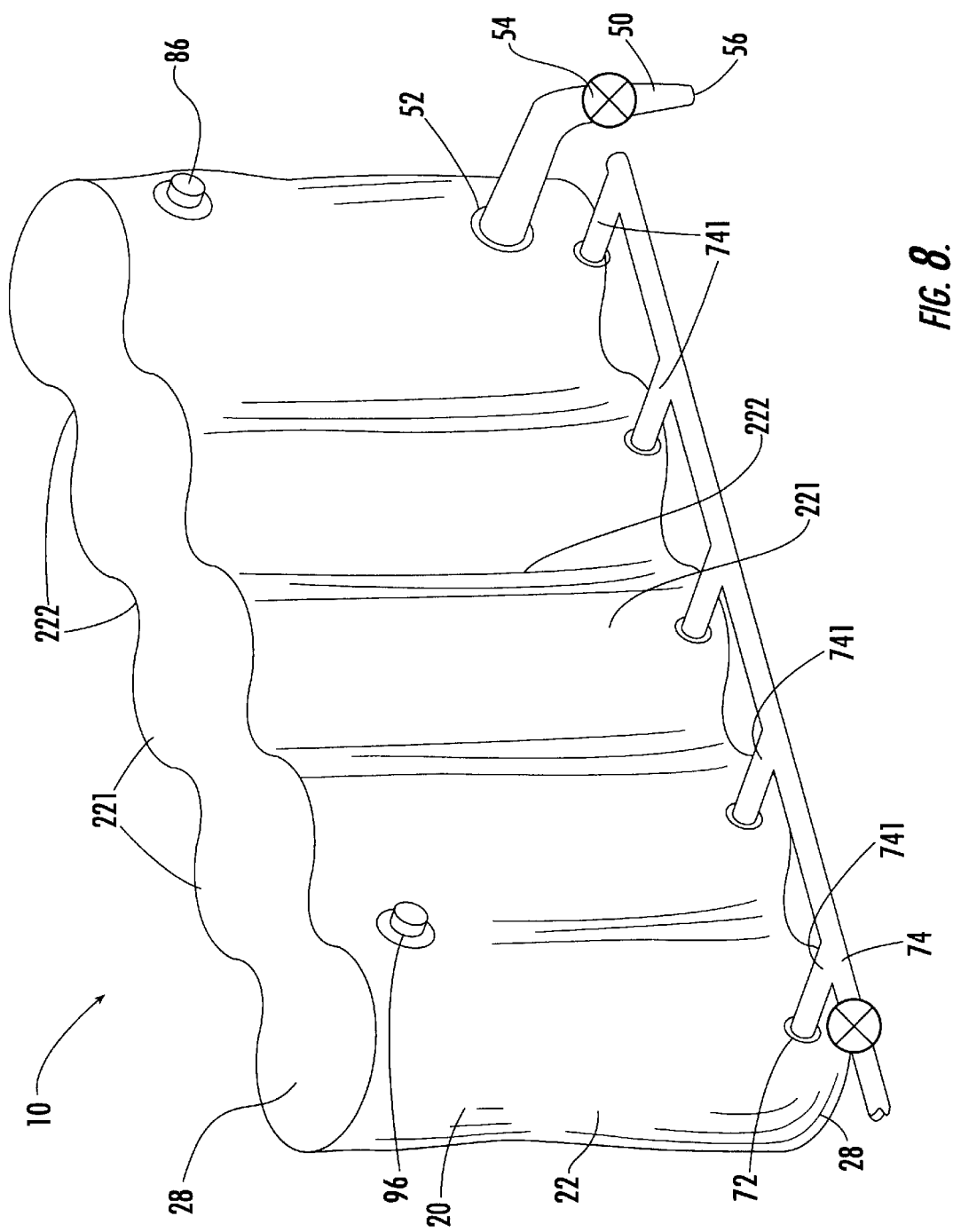
FIG. 8 illustrates the embodiment of FIG. 6 in perspective view.

The said container (20) may be formed by fusion bonding two suitable sheets of suitable material, as hereinbefore exampled, along predetermined seams. Referring to the first and second embodiments for example, two sheets (200) of material may be cut in an approximately elongated rectangular shape and superposed one over the other, FIG. 4. The sheets are then fusion bonded together in a manner well known in the art to form seams along the peripheries (205) and (206) of the two longer sides, and along the periphery of one of the shorter ends (210), and again parallel and inwardly displaced thereto to form a seam (220) at the upper end of the container (20). The fusion weld seams (207) and (208) along the long sides and situated between these parallel short end seams (210) and (220) may be cut off or otherwise removed, effectively leaving a loop of material (27). The bottom end (28) of the container (20) is formed by fusion bonding the remaining short end of the sheets along two sloping seam lines, (230) and (240), mutually converging from the seams (205) and (206) of the long sides. Optionally, the two sloping seam lines (230) and (240) may be joined above the apex by another fusion welded seam line (260) approximately orthogonal to the long side seams (205) and (206). Prior to fusion welding the two sheets together, rigid plastic bosses (270), (290), (280) and (250) may be fusion welded at locations corresponding to the said air inlet means, gas outlet means, additive inlet means and harvesting means, respectively. These bosses provide suitable mechanical attachment points for each of the corresponding input and output means. The third, fourth and fifth embodiments of the present invention may be manufactured in a similar manner to the first and second embodiments, substantially as described above, mutatis mutandis.

In all embodiments, the device (10) is made from a material or materials that are biologically compatible and which enable the container to be sterilised prior to first use.

The present invention also relates to a battery of disposable devices for axenically culturing and harvesting cells and/or tissue in cycles, wherein each of a plurality of these devices is structurally and operationally similar to said device (10), hereinbefore defined and described with reference to the first through the fifth embodiments thereof.

Figure 10:
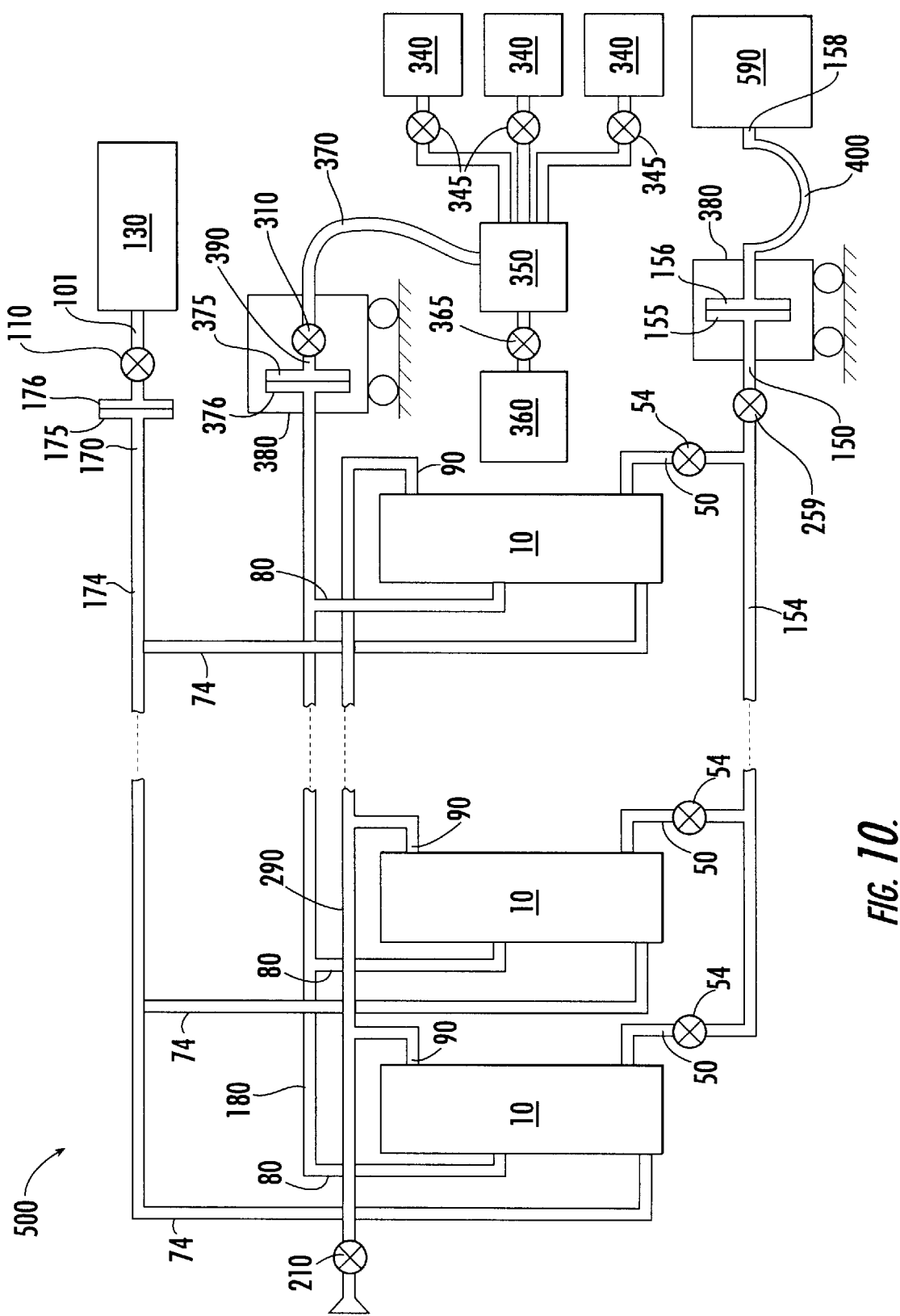
FIG. 10 illustrates the main components of a preferred embodiment of the battery of the present invention comprising a plurality of devices of any one of FIGS. 1 to 8.

Referring to FIG. 10, a battery (500) comprises a plurality of said devices (10), as hereinbefore described with respect to any one of the first through the fifth embodiments, which are held on a frame or frames (not shown) by means of said attachment means or said support structure (400), for example. Typically, the battery (500) may be divided into a number of groups, each group comprising a number of devices (10).

In the preferred embodiment of the said battery (500), the said air inlet means of the devices (10) in each group are interconnected. Thus the said air inlet pipes (74) of each device (10) of the group is connected to common piping (174) having a free end (170), which is provided with an aseptic connector (175). Sterilised air is provided by a suitable air compressor (130) having a suitable sterilising means (110) such as one or more filters. The compressor (130) comprises a delivery pipe (101) having an aseptic connector (176) at its free end which is typically connectable to the said aseptic connector (175) located at the free end of common piping (174). This connection is made at the beginning of each run of growth/harvesting cycles in a mobile sterile hood (380) to ensure that sterile conditions are maintained during the connection. The sterile hood (380) provides a simple relatively low-cost system for connecting the various services, such as air, media, inoculant and harvested cells, to and from the group of devices (10) under substantially sterile conditions. Similarly, at the end of each run of growth/harvesting cycles, the connectors (175) and (176) are disconnected in the sterile hood (380), and the used devices are discarded, allowing the connector (175) at the compressor end to be connected to the connector (176) of a new group of devices. Sterilised air is typically provided continuously, or alternatively in predetermined pulses, during each culturing cycle.

In the preferred embodiment of the said battery (500), excess air and/or waste gases from each of the said devices (10) is removed to the atmosphere via common piping (290) suitably connected to each corresponding gas outlet means (90). Said common piping (290) is provided with suitable means (210), such as one or more filters, for preventing contaminants from flowing into said devices (10). Alternatively, the gas outlet means (90) of each device (10) may be individually allowed to vent to the atmosphere, preferably via suitable filters which substantially prevent contaminants from flowing into the device (10).

Media and additives are contained in one or more holding tanks (340). For example, micro elements, macro elements and vitamins may be held in different tanks, while additives such as antibiotics and fungicides may also held in yet other separate tanks. Pumping means (345) serving each tank enable the desired relative proportions of each component of the media and/or additives to be delivered at a predetermined and controllable flow rate to a static mixer (350), through which water—either distilled or suitably filtered and purified—flows from a suitable supply (360), preferably with the aid of a suitable pumping means (365) (FIG. 10). By adjusting the flow rates of pumping means (345) and (365), for example, the concentration of media as well as additives available to be delivered into said devices (10) may be controlled. Media and/or additives mixed with water may then be delivered from the said static mixer (350) under sterile conditions via a filter (310) and a delivery pipe (370) having an aseptic connector (375) as its free end (390).

In the preferred embodiment of the said battery (500), the inlet of additive pipe (80) of each corresponding device (10) in the group of said devices, are interconnected via common piping (180), which comprises at its free end a common aseptic connector (376). Said common aseptic connector (376) may then be connected, in the said sterile hood (380), to the aseptic connector (375) at the free end (390) of the media and additive pipe (370), thus enabling each device (10) of the battery, or of the group, to be supplied with media and additives. At the end of the life of the devices (10), and prior to discarding the same, the aseptic connectors (375) and (376) are disconnected in the sterile hood. The aseptic connector (375) is then ready to be connected to the new aseptic connector (376) of the next sterilised group of new devices (10) of the battery, ready for the next run of culturing/harvesting cycles.

The sterile hood (380) may also be utilised for connecting the media/additives tank (350) to each one of a number of groups of devices (10) in the battery, in turn, during the useful lives of the devices in these groups. Thus, when one group of devices has been serviced with media/additives, the aseptic connector (376) of this group is aseptically sealed temporarily in the sterile hood (380), which is then moved to the next group of devices where their common aseptic connector (376) is connected to the sterile connector (375) of the pipe (370), thus enabling this group of devices to be serviced with media/additives.

In a different embodiment of the said battery (500), said mobile sterile hood (380) may be used to connect together the free end (390) of a preferably flexible delivery pipe connected to said static mixing tank (350), to the additive inlet means of each device (10) in turn. The said sterile hood (380) may then be moved from one said device (10) to the next, each time the said end (390) being connected to the inlet end of the corresponding pipe (80) to enable media to be provided to each device in turn. The sterile hood (380), together with aseptic connecting means, preferably made from stainless steel, at said end (390) and the inlet of the pipe (80) of the corresponding device (10), respectively, enable each device (10) to be easily connected and subsequently disconnected to the end (390) and thus to the media supply, under sterile conditions. Many other examples of suitable connecting means for connecting two pipes together are well known in the art. Suitable filters are provided at the end (390) and at the pipe (80), respectively, to prevent or at least minimise potential contamination of the container contents. The sterile hood (380) may thus be automatically or manually moved from device (10) to device (10), and at each device in turn, an operator may connect the device (10) to the media supply using the sterile hood (380), fill the device with a suitable quantity of media and/or additives, and subsequently disconnect the sterile hood (380) from the device, to then move on to the next device. Of course, the end (390) may be adapted to comprise a plurality of connecting means (375) rather than just a single sterilised connecting means (375), so that rather than one, a similar plurality of devices (10) having corresponding connecting means (376) may be connected at a time to the media supply via the trolley (380).

Each time, prior to connecting said end (390) to each device or set or group of devices, the corresponding connecting means (375) and (376) are typically autoclave sterilised.

In yet another embodiment of the battery (500), a single pipe or a set of pipes (not shown) connect said static mixer (350), to one said device (10) or to a corresponding set of devices (10), respectively, at a time, wherein a conveyor system transports the device (10) or set of devices (10) to the said single pipe or set of pipes, respectively, or vice versa. After filling the said device (10) or set of devices (10), the conveyor enables a further device (10), or a further set of devices (10) to be connected to the static mixer (350) by means of the said single pipe or set of pipes, respectively.

In the preferred embodiment of the said battery (500), the harvesting means of each of the devices (10) of the group are interconnected. Thus the harvesting pipes (50) of each said device (10) is connected to common harvesting piping (154) having a free end (150), which is provided with an aseptic connector (155). Preferably, each of the said harvesting pipes (50) may comprise a valve (54), as hereinbefore described, to close off or permit the flow of harvested cells from each corresponding device (10). Thus, for example, if it is determined that a number of devices in a particular group are contaminated, while the other devices are not, then the cells in these latter devices may be harvested without fear of contamination from the former devices, so long as the valves (54) of the contaminated devices remain closed. Preferably, said common piping further comprises a common shut-off valve (259) upstream of the said aseptic connector (155). Preferably, said contamination prevention means is provided for substantially preventing introduction of contaminants into said container via said harvesting means after harvesting. In the preferred embodiment, said contamination prevention means comprises a substantially U-shaped fluid trap (400), having an aseptic connector (156) at one arm thereof, the other arm having an opening (158) in fluid communication with a receiving tank (590). The aseptic connectors (155) and (156) are then interconnected in the said mobile sterile hood (380) under sterile conditions. Harvesting is then effected by opening the valves (54) of all the devices in the group which are not contaminated, as well as common valve (259). Cells from the group will then flow into the receiving tank (590), preferably under gravity, though in some cases a suitable pump may be used. After harvesting is completed, the aseptic connectors (155) and (156) may be disconnected in the said sterile hood (380), which can then be moved to the next group of devices (10): the corresponding aseptic connector (155) of this group may then be interconnected with aseptic connector (156) of the U-tube (400), and thereby enable the cells of this group of devices to be harvested.

In another embodiment of the said battery (500), a single pipe or a set of pipes (not shown) may connect said common receiving tank to a said device (10) or a corresponding set of devices (10), respectively, at a time, wherein a conveyor system transports the device (10) or set of devices (10) to the said single pipe or set of pipes, respectively, or vice versa. After harvesting the said device (10) or set of devices (10), the conveyor enables a further device (10) or set of devices (10) to be connected to the said common receiving tank by means of the said single pipe or set of pipes, respectively.

In another embodiment of the said battery (500), each device (10) may be individually harvested, wherein the said harvesting means of each device comprises said contamination prevention means for substantially preventing introduction of contaminants into said container via said harvesting means after harvesting. In this embodiment, said contamination prevention means comprises said U-shaped fluid trap (400) as hereinbefore described, having an aseptic connector (156) at one arm thereof, the other arm having an opening (158) in fluid communication with a receiving tank (590). The said harvesting means comprises an aseptic connector (55) which may be connected to the aseptic connector (156) of the fluid trap (400) in the said mobile sterile hood (380) under sterile conditions. Harvesting is then effected by opening the valve (54) of the device, wherein cells will then flow into the receiving tank, preferably under gravity, though in some cases a suitable pump may be used. After harvesting is completed, these aseptic connectors, (55) and (156), may be disconnected in the said sterile hood (380), which can then be moved to the next device (10): the corresponding aseptic connector (55) of the harvesting means of this device may then be interconnected with aseptic connector (156) of the U-tube (400), and thereby enable the cells of this next device to be harvested.

In the preferred embodiment of the said battery (500), said harvesting means may also be used for initially providing inoculant at the start of a new run of growth/harvesting cycles. Thus, inoculant may be mixed with sterilised medium in a suitable tank having a delivery pipe comprising at its free end an aseptic connector which is connected to the said aseptic connector (155) of the common harvesting piping (154) in the said sterile hood (380). Inoculant may then be allowed to flow under gravity, or with the aid of a suitable pump, to each of the devices (10) of the group via said common harvesting piping (154), after which the aseptic connectors are disconnected in the sterile hood.

Alternatively, the said inoculant may be introduced into the devices via the said additive inlet means, in particular the said additive means common piping (180), in a similar manner to that hereinbefore described regarding the harvesting means and the common harvesting piping (155), mutatis mutandis.

The present invention also relates to a method for culturing and harvesting cells and/or tissue in a multiple-use disposable device comprising the steps of:
  a) providing said device (10), hereinbefore defined;
  b) providing sterile air to said container via said air inlet means during each cycle, either continuously or in pulses;
  c) providing sterile said culture medium and/or sterile said additives via said additive inlet means;
  d) providing axenic inoculant via said harvesting means;
  e) optionally illuminating said container with external light means;
  f) allowing said cells and/or tissue to grow in said medium to a desired yield;
  g) continuously allowing excess air and/or waste gases to leave said container via said gas outlet means;
  h) checking for contaminants and/or the quality of the cells/tissues which are produced in said container: if contaminants are found to be present or the cells/tissues which are produced are of poor quality, the device and its contents are disposed of; if contaminants are not found, step i) is executed;
  i) harvesting at least said desired first portion of the said medium containing cells and/or tissue, while leaving a remaining said second portion of medium containing cells and/or tissue in said container, wherein said second portion of medium may serve as inoculant for a next culture/harvest cycle;
  j) providing sterile said culture medium and/or sterile said additives for the next culture/harvest cycle via said additive inlet means;
  k) repeating steps b), e), f), g), h), i) and j) a plurality of times until in h) the said contaminants are found to be present or the cells/tissues which are produced are of poor quality, whereupon the device and its contents are disposed of.

The present invention also relates to a method for axenically culturing and harvesting cells and/or tissue anerobically in a battery of disposable devices comprising the steps of:
  a) providing a battery (500) of at least one group of said devices (10), wherein said devices do not comprise air inlet means, and for at least one said device (10) thereof:
  b) providing axenic inoculant to said device via said common harvesting piping;
  c) providing sterile said culture medium and/or sterile said additives to said device via said common additive inlet piping;
  d) optionally illuminating said device with external light means;
  e) allowing said cells and/or tissue in said device to grow in said medium to a desired yield;
  f) allowing excess air and/or waste gases to leave said device continuously via said common gas outlet piping;
  g) checking for contaminants and/or the quality of the cells/tissues which are produced in said device: if in the said device contaminants are found or the cells/tissues which are produced are of poor quality, the said harvesting means of said device is closed off preventing contamination of other said devices of said battery; if in all of the said devices of the said battery contaminants are found or the cells/tissues which are produced therein are of poor quality, all the devices and their contents are disposed of; if contaminants are not found and the quality of the produced cells/tissues is acceptable, the device is considered harvestable and step h) is executed;
  h) for each said harvestable device of step g), harvesting at least said desired first portion of the said medium containing cells and/or tissue via said common harvesting piping and said contamination prevention means to a suitable receiving tank, while leaving said second portion of medium containing cells and/or tissue in said container, wherein said second portion of medium serves as inoculant for a next culture/harvest cycle;
  i) providing sterile said culture medium and/or sterile said additives for the next culture/harvest cycle via said additive inlet means;
  j) repeating steps d), e), f), g), h) and i) a plurality of times until in g) the said contaminants are found or the cells/tissues which are produced are of poor quality for all of the said devices of the said battery, whereupon the said contamination prevention means are disconnected from the said common harvesting means and the said devices and their contents are disposed of.

The present invention also relates to a method for axenically culturing and harvesting cells and/or tissue aerobically in a battery of disposable devices comprising the steps of:
  a) providing a battery (500) of at least one group of said devices (10), wherein said devices comprise air inlet means as hereinbefore described, and for at least one said device (10) thereof:
  b) providing axenic inoculant to said device via said common harvesting piping;
  c) providing sterile said culture medium and/or sterile said additives to said device via said common additive inlet piping;
  d) providing sterile air to said device via said common air inlet piping;
  e) optionally illuminating said device with external light means;

f) allowing said cells and/or tissue in said device to grow in said medium to a desired yield;

g) allowing excess air and/or waste gases to leave said device continuously via said common gas outlet piping;

h) checking for contaminants and/or the quality of the cells/tissues which are produced in said device: if in the said device contaminants are found or the cells/tissues which are produced are of poor quality, the said harvesting means of said device is closed off preventing contamination of other said devices of said battery; if in all the said devices of the said battery contaminants are found or the cells/tissues which are produced therein are of poor quality, all the devices and their contents are disposed of; if contaminants are not found and the quality of the produced cells/tissues is acceptable, the device is considered harvestable and step i) is executed;

i) for each said harvestable device of step h), harvesting at least said desired first portion of the said medium containing cells and/or tissue via said common harvesting piping and said contamination prevention means to a suitable receiving tank, while leaving said second portion of medium containing cells and/or tissue in said container, wherein said second portion of medium serves as inoculant for a next culture/harvest cycle;

j) providing sterile said culture medium and/or sterile said additives for the next culture/harvest cycle via said additive inlet means;

k) repeating steps d), e), f), g), h), i) and j) a plurality of times until in h) the said contaminants are found or the cells/tissues which are produced are of poor quality for all of the said devices of the said battery, whereupon the said contamination prevention means are disconnected from the said common harvesting means and the said devices and their contents are disposed of.

Typically, a water purification system supplies deionised and pyrogen free water to a tank comprising concentrated media, and diluted media is then pumped to the said device (10) via said additive inlet means. Filters, typically 0.2 μm, are installed in the feed pipes and also just upstream of the said additive inlet means to minimise risk of contamination of the container contents in each device (10). Alternatively or additionally, a one-way valve may be also used to minimise this risk.

For the first culturing cycle of each device (10), inoculant, typically a sample of the type of cell that it is required to harvest in the said device (10), is premixed with media or water in a steam sterilised container and is introduced into the device (10) via the harvesting means. Media is then introduced into the device (10) via said additive input means. For subsequent cycles, only media and/or additives are introduced, as hereinbefore described.

Typically, an air compressor provides substantially sterilised air to each said device (10), via a number of filters: a coarse filter for removing particles, a dryer and humidity filter for removing humidity, and a fine filter, typically 0.2 μm, for removing contaminants. Preferably, another filter just upstream of the said air inlet means further minimises the risk of contamination of the container contents.

For each said device (10), all connections to the container (20), i.e., to said air inlet means, to said additive inlet means, and preferably also to the gas outlet means and to the harvesting means are autoclave sterilised prior to use, and sterility is maintained during connection to peripheral equipment, including, for example, said air supply and said exhaust means by performing the connections in the sterile hood as hereinbefore described.

Temperature control for each device (10) is preferably provided by suitable air conditioning means. Optional illumination of the device may be provided by suitable fluorescent light means suitably arranged around the said device (10), when required for cell growth.

During each culturing cycle of each device (10), the contents of each corresponding container (20) are typically aerated and mixed for about 7 to about 14 days, or longer, under controlled temperature and lighting conditions.

At the end of the culturing cycle for each device (10), the corresponding said harvesting means is typically connected to a presterilised environment by means of suitable connectors which are sterilised prior and during connection, as hereinbefore described. Harvesting is then effected, leaving behind between about 2.5% to about 45%, though typically between about 10% to about 20%, of cells and/or tissue to serve as inoculant for the next cycle.

The harvested cells/tissues may then be dried, or extracted, as required.

The present invention will be described in more detail with reference to the following example, which is not intended to limit the scope of the invention.

A group of 10 bioreactors (each a device according to the invention), each with a container made from polyethylene-nylon copolymer, (0.1 mm wall thickness, 20 cm diameter, 1.2 m height), complete with 30 mm ports at 5 cm (for air inlet means), 25 cm (for harvesting means), 68 cm (additive inlet means), and 90 cm (gas outlet means) from the bottom, effective fillable volume about 10 liters was used. The bioreactors, together with their fittings, were sterilized by gamma irradiation (2.5 mRad).

Nine liters of Schenk & Hildebrandt mineral/vitamin medium, 2 mg/l each of chlorophenoxyacetic acid and 2,4-dichlorophenoxyacetic acid, 0.2 mg/l kinetin, 3% sucrose, and 900 ml packed volume initial inoculum of line V24 Catharanthus roseus (Vinca) cells were introduced into each bioreactor. The volume of air above the surface of the medium was 3 l. Aeration was carried out using a flow volume of 1.5 l/min sterile air, provided through a 4 mm orifice (air inlet means), located 1 cm from the bottom of the container.

The bioreactors were mounted in a controlled temperature room (25° C.) and culturing was continued for 10 days, until the packed volume increased to about 7.5 l (75% of the total volume; a doubling rate of 2 days during the logarithmic phase). At this time point, cells were harvested by withdrawing 9 liters of medium and cells through the harvesting means and 9 liters of fresh sterile medium together with the same additives were added via the additive inlet means. Cells were again harvested as above at 10-day intervals, for 6 additional cycles, at which time the run was completed.

A total weight of 6.5 kg fresh cells (0.5 kg dry weight) was thus collected over seven 10-day periods of time, from each of the 10 l capacity bioreactors. These cells had a 0.6% content of total alkaloids, the same as the starting line.

Although only a few embodiments have been described in detail in the foregoing description, the present invention is not limited thereto and is only defined by the scope of the claims.

What is claimed is:

1. A disposable device for axenically culturing and harvesting at least one of tissue and a quantity of cells in at least one cycle, said device comprising a sterilisable disposable non-rigid container which is at least one of transparent and translucent, said container having a top end and a bottom end, which container may be at least partially filled with at least one of a suitable sterile biological cell culture medium, a suitable sterile biological tissue culture medium, axenic inoculant, sterile air and required other sterile additives, said container comprising:
  (i) gas outlet means for removing at least one of excess air and waste gases from said container;
  (ii) additive inlet means for introducing at least one of said inoculant, said culture medium and said additives into said container;
and characterized in further comprising
  (iii) reusable harvesting means comprising suitable flow control means for enabling harvesting of at least a desired portion of said medium containing at least one of said tissues and quantity of cells, when desired, thereby enabling said device to be used continuously for at least one further consecutive culturing/harvesting cycle,
wherein a remainder of said medium containing at least one of said cells and tissue, remaining in said device from a previous harvested cycle, may serve as inoculant for a next culture and harvest cycle, wherein at least one of said culture medium and said required additives are provided.

2. The device as claimed in claim 1, further comprising air inlet means for introducing sterile air in the form of bubbles into said culture medium through a first inlet opening, wherein said air inlet means is connectable to a suitable air supply.

3. The device as claimed in claim 1, said harvesting means comprising contamination prevention means for substantially preventing introduction of contaminants into said container via said harvesting means.

4. The device as claimed in claim 1, wherein said container is made from a non-rigid plastics material.

5. The device as claimed in claim 4, wherein said material is selected from the group comprising polyethylene, polycarbonate, a copolymer of polyethylene and nylon, PVC and EVA.

6. The device as claimed in claim 4, wherein said container is made from a laminate of more than one layer of said materials.

7. The device as claimed in claim 4, wherein said container is formed by fusion bonding two suitable sheets of said material along predetermined seams.

8. The device as claimed in claim 2, wherein said air inlet means comprises an air inlet pipe extending from said inlet opening to a location inside said container at or near the said bottom end thereof.

9. The device as claimed in claim 2, wherein said at least one air inlet means comprises a least one air inlet pipe connectable to a suitable air supply and in communication with a plurality of secondary inlet pipes, each said secondary inlet pipe extending to a location inside said container, via a suitable inlet opening therein, for introducing sterile air in the form of bubbles into said culture medium.

10. The device as claimed in claim 9, wherein said device comprises a substantially box-like geometrical configuration, having an overall length, height and width.

11. The device as claimed in claim 10, wherein the height-to-length ratio is between about 1 and about 3, and preferably about 1.85.

12. The device as claimed in claim 10, wherein the height to width ratio is between about 5 and about 30, and preferably about 13.

13. A disposable device for axenically culturing and harvesting at least one of tissue and a quantity of cells in at least one cycle, said device comprising a sterilisable disposable container which is at least one of transparent and translucent, said container having a top end and a bottom end, said device further comprising a substantially boxlike geometrical configuration, having an overall length, height and width, wherein the height-to-length ratio is between about 1 and about 3, said device further comprising a support aperture substantially spanning the depth of said device, said aperture adapted to enable said device to be supported on a suitable pole support wherein said container may be at least partially filled with at least one of a suitable sterile biological cell culture medium, a suitable sterile biological tissue culture medium, axenic inoculant, sterile air and required other sterile additives, said container comprising:
  (i) gas outlet means for removing at least one of excess air and waste gases from said container;
  (ii) additive inlet means for introducing at least one of said inoculant, said culture medium and said additives into said container;
and characterized in further comprising
  (iii) at least one air inlet means for introducing sterile air in the form of bubbles into said culture medium through a first inlet opening, said at least one air inlet means comprising at least one air inlet pipe connectable to a suitable air supply and in communication with a plurality of secondary inlet pipes, each secondary inlet pipe extending to a location inside said container, via a suitable inlet opening therein, for introducing sterile air in the form of bubbles into said culture medium, and
  (iv) reusable harvesting means comprising suitable flow control means for enabling harvesting of at least a desired portion of said medium containing at least one of said tissues and quantity of cells, when desired, thereby enabling said device to be used continuously for at least one further consecutive culturing/harvesting cycle,
wherein a remainder of said medium containing at least one of said cells and tissue, remaining from a previous harvested cycle, may serve as inoculant for a next culture and harvest cycle, wherein at least one of said culture medium and said required additives are provided.

14. A disposable device for axenically culturing and harvesting at least one of tissue and a quantity of cells in at least one cycle, said device comprising a sterilisable disposable container which is at least one of transparent and translucent, having a top end and a bottom end, which container may be at least partially filled with at least one of a suitable sterile biological cell culture medium, a suitable sterile biological tissue culture medium, axenic inoculant, sterile air and required other sterile additives, said container comprising:
  (i) gas outlet means for removing at least one of excess air and waste gases from said container;
  (ii) additive inlet means for introducing at least one of said inoculant, said culture medium and said additives into said container;
and characterized in further comprising
  (iii) at least one air inlet means for introducing sterile air in the form of bubbles into said culture medium through a first inlet opening, said at least one air inlet means comprising at least one air inlet pipe connectable to a suitable air supply and in communication with a plurality of secondary inlet pipes, each secondary inlet pipe extending to a location inside said container, via a suitable inlet opening therein, for introducing sterile air in the form of bubbles into said culture medium, said device further comprising a support structure for supporting said device; and (iv) reusable harvesting means comprising suitable flow control means for enabling harvesting of at least a desired portion of said medium containing at least one of said tissues and quantity of cells, when desired, thereby enabling said device to be used continuously for at least one further consecutive culturing/harvesting cycle, wherein a remainder of said medium containing at least one of said cells and tissue, remaining from a previous harvested cycle, may serve as inoculant for a next culture and harvest cycle, wherein at least one of said culture medium and said required additives are provided.

15. The device as claimed in claim 14, wherein said support structure comprises a pair of opposed frames, each said frame comprising upper and lower support members spaced by a plurality of substantially parallel vertical support members suitably joined to the said upper and lower support members.

16. The device as claimed in claim 15, wherein said plurality of vertical support members consists of at least one said vertical support member at each longitudinal extremity of the said upper and lower support members.

17. The device as claimed in claim 15, wherein said frames are spaced from each other by a plurality of spacing bars releasably or integrally joined to said frames.

18. The device as claimed in claim 16, wherein said spacing bars are strategically located such that the said device may be inserted and removed relatively easily from the said support structure.

19. The device as claimed in claim 15, wherein the said lower support member of each said frame comprises at least one lower support adapted for receiving and supporting a corresponding portion of the said bottom end of the said device.

20. The device as claimed in claim 19, wherein each said lower support is in the form of suitably shaped tab projecting from each of the lower support members in the direction of the opposed frame.

21. The device as claimed in claim 15, wherein said frames each comprise at least one interpartitioning means projecting from each frame in the direction of the opposed frame, for to pushing against the sidewall of said device at a predetermined position, such that opposed pairs of said interpartitioning means effectively reduce the width of the said device at said predetermined position.

22. The device as claimed in claims 21, wherein said interpartitioning means comprise suitable substantially vertical members spaced from the said upper and lower support members in a direction towards the opposed frame by means of suitable upper and lower struts.

23. The device as claimed in claim 14, wherein, said support structure may comprise a plurality of castors for transporting the said devices.

24. The device as claimed in claim 1, wherein said container comprises a suitable filter mounted on said gas outlet means for substantially preventing introduction of contaminants into said container via said gas outlet means.

25. The device as claimed in claim 1, wherein said container further comprises a suitable filter mounted on said additive inlet means for substantially preventing introduction of contaminants into said container via said additive inlet means.

26. A disposable device for axenically culturing and harvesting at least one of tissue and a quantity of cells in at least one cycle, said device comprising a sterilisable disposable container which is at least one of transparent and translucent, having a top end and a bottom end, which container may be at least partially filled with at least one of a suitable sterile biological cell culture medium, a suitable sterile biological tissue culture medium, axenic inoculant, sterile air and required other sterile additives, said container comprising:

(i) gas outlet means for removing at least one of excess air and waste gases from said container;

(ii) additive inlet means for introducing at least one of said inoculant, said culture medium and said additives into said container;

and characterized in further comprising (iii) reusable harvesting means comprising suitable flow control means for enabling harvesting of at least a desired portion of said medium containing at least one of said tissues and quantity of cells, when desired, thereby enabling said device to be used continuously for at least one further consecutive culturing/harvesting cycle, said reusable harvesting means further comprising a contamination prevention means comprising a U-shaped fluid trap, wherein one arm thereof is aseptically mounted to an external outlet of said harvesting means by suitable aseptic connection means, wherein a remainder of said medium containing at least one of said cells and tissue, remaining from a previous harvested cycle, may serve as inoculant for a next culture and harvest cycle, wherein at least one of said culture medium and said required additives are provided.

27. A disposable device for axenically culturing and harvesting at least one of tissue and a quantity of cells in at least one cycle, said device comprising a sterilisable disposable container which is at least one of transparent and translucent, having a top end and a bottom end, which container may be at least partially filled with at least one of a suitable sterile biological cell culture medium, a suitable sterile biological tissue culture medium, axenic inoculant, sterile air and required other sterile additives, said container comprising:

(i) gas outlet means for removing at least one of excess air and waste gases from said container;

(ii) additive inlet means for introducing at least one of said inoculant, said culture medium and said additives into said container;

and characterized in further comprising (iii) reusable harvesting means located at the bottom of said bottom end of said container, said harvesting means further comprising suitable flow control means for enabling harvesting of at least a desired portion of said medium containing at least one of said tissues and quantity of cells when desired, thereby enabling said device to be used continuously for at least one further consecutive culturing/harvesting cycle, wherein a remainder of said medium containing at least one of said cells and tissue, remaining from a previous harvested cycle, may serve as inoculant for a next culture and harvest cycle, wherein at least one of said culture medium and said required additives are provided.

28. A disposable device for axenically culturing and harvesting at least one of tissue and a quantity of cells in at least one cycle, said device comprising a sterilisable disposable container which is at least one of transparent and translucent, having a top end and a bottom end, which container may be at least partially filled with at least one of a suitable sterile biological cell culture medium, a suitable sterile biological tissue culture medium, axenic inoculant, sterile air and required other sterile additives, said container comprising:

(i) gas outlet means for removing at least one of excess air and waste gases from said container;

(ii) additive inlet means for introducing at least one of said inoculant, said culture medium and said additives into said container;

and characterized in further comprising (iii) reusable harvesting means located near the bottom of said bottom end of said container, said harvesting means further comprising suitable flow control means for enabling harvesting of at least a desired portion of said medium containing at least one of said cells and tissues when desired, thereby enabling said device to be used continuously for at least one further consecutive culturing/harvesting cycle, wherein said harvesting means is positioned such that at the end of each harvesting cycle a remainder of said medium containing at least one of said cells and tissue automatically remains at said bottom end of said container up to a level below the level of said harvesting means, said remainder of said medium containing at least one of said cells and tissue, may serve as inoculant for a next culture and harvest cycle, wherein at least one of said culture medium and said required additives are provided.

29. The device as claimed in claim 1, wherein said bottom end is substantially convex.

30. The device as claimed in claim 1, wherein said bottom end is substantially frusta-conical.

31. The device as claimed in claim 1, wherein said container comprises an internal fillable volume of between about 5 liters and about 200 liters.

32. A disposable device for axenically culturing and harvesting at least one of tissue and a quantity of cells tissue in at least one cycle, said device comprising a sterilisable disposable container which is at least one of transparent and translucent, having a top end and a bottom end, which container may be at least partially filled with at least one of a suitable sterile biological cell culture medium, a suitable sterile biological tissue culture medium, axenic inoculant, sterile air and required other sterile additives, said container comprising:

(i) gas outlet means for removing at least one of excess air and waste gases from said container;

(ii) additive inlet means for introducing at least one of said inoculant, said culture medium and said additives into said container;

and characterized in further comprising (iii) reusable harvesting means comprising suitable flow control means for enabling harvesting of at least a desired portion of said medium containing at least one of said tissue and quantity of cells when desired, thereby enabling said device to be used continuously for at least one further consecutive culturing/harvesting cycle, wherein a remainder of said medium containing at least one of said cells and tissue, remaining from a previous harvested cycle, may serve as inoculant for a next culture and harvest cycle, wherein at least one of said culture medium and said required additives are provided and said device further comprises suitable attachment means for attaching said device to a suitable support structure.

33. The device as claimed in claim 32, wherein said attachment means comprises a loop of suitable material preferably integrally attached to said top end of said container.

34. A battery of disposable devices, comprising at least two of said disposable devices for axenically culturing and harvesting at least one of tissue and a quantity of cells in at least one cycle, each of said devices comprising a sterilisable disposable container which is at least one of transparent and translucent, having a top end and a bottom end, which container may be at least partially filled with at least one of a suitable sterile biological cell culture medium, a suitable sterile biological tissue culture medium, axenic inoculant, sterile air and required other sterile additives, said container comprising:

(i) gas outlet means for removing at least one of excess air and waste gases from said container;

(ii) additive inlet means for introducing at least one of said inoculant, said culture medium and said additives into said container;

and characterized in further comprising (iii) reusable harvesting means comprising suitable flow control means for enabling harvesting of at least a desired portion of said medium containing at least one of said tissue and quantity of cells when desired, thereby enabling said device to be used continuously for at least one further consecutive culturing/harvesting cycle, and (iv) an air inlet means for introducing sterile air in the form of bubbles into said culture medium through a first air inlet opening, said air inlet means connectable to a suitable air supply, wherein a remainder of said medium containing at least one of said cells and tissue, remaining from a previous harvested cycle, may serve as inoculant for a next culture and harvest cycle, wherein at least one of said culture medium and said required additives are provided.

35. The battery as claimed in claim 34, wherein said devices are supported by a suitable support structure via the said attachment means of each said device.

36. The battery as claimed in claim 34, wherein the said gas outlet means of each said device is suitably connected to a common gas outlet piping which optionally comprises suitable means for preventing contaminants from flowing into said devices.

37. The battery as claimed in claim 36, wherein said means for preventing contaminants from flowing into said devices comprises a suitable filter.

38. The battery as claimed in claim 34, wherein the said additive inlet means of each said device is suitably connected to a common additive inlet piping having a free end optionally comprising suitable aseptic connecting means thereat.

39. The battery as claimed in claim 38, wherein said free end is connectable to a suitable supply of medium and/or additives.

40. The battery as claimed in claim 34, wherein the said harvesting means of each said device is suitably connected to a common harvesting piping having a free end optionally comprising suitable aseptic connecting means thereat.

41. The battery as claimed in claim 40, further comprising contamination prevention means for substantially preventing introduction of contaminants into said container via said common harvesting piping.

42. The battery as claimed in claim 41, wherein said contamination prevention means comprises a U-shaped fluid trap, wherein one arm thereof is free having an opening and wherein the other end thereof is aseptically mountable to said free end of said common harvesting piping via suitable aseptic connection means.

43. The battery as claimed in claims 42, wherein the said free end of said U-tube is connectable to a suitable receiving tank.

44. The battery as claimed in claim 34, wherein the said air inlet means of each said device is suitably connected to a common air inlet piping having a free end optionally comprising suitable aseptic connecting means thereat.

45. The battery as claimed in claim 44, wherein said free end is connectable to a suitable air supply.

46. A method for axenically culturing and harvesting at least one of tissue and a quantity of cells in a disposable device comprising the steps of:
   a) providing said device which comprises a sterilisable disposable container which is at least one of transparent and translucent, having a top end and a bottom end, which container may be at least partially filled with at least one of a suitable sterile biological cell culture medium, a suitable sterile biological tissue culture medium, axenic inoculant, sterile air and other sterile required additives, said container comprising:
      (i) gas outlet means for removing at least one of excess air and waste gases from said container;
      (ii) additive inlet means for introducing at least one of said inoculant, said culture medium and said additives into said container;
      (iii) reusable harvesting means comprising suitable flow control means for enabling harvesting of at least a portion of said medium containing at least one of said tissue and quantity of cells when desired, thereby enabling said device to be used continuously for at least one further consecutive cycle, wherein a remainder of said medium containing at least one of said cells and tissue, remaining from a previously harvested cycle may serve as inoculant for a next culture and harvest cycle, wherein at least one of said culture medium and said required additives are provided;
   b) providing axenic inoculant via said harvesting means;
   c) providing sterile at least one of said culture medium and said additives via said additive inlet means;
   d) optionally illuminating said container with external light means;
   e) allowing at least one of said cells and tissue to grow in said medium to a desired yield;
   f) allowing at least one of excess air and waste gases to leave said container continuously via said gas outlet means;
   g) checking for at least one of contaminants and the quality of at least one of the cells and tissues which are produced in said container: if contaminants are found or at least one of the cells and tissues which are produced are of poor quality, the device and its contents are disposed of; if contaminants are not found, step h) is executed;
   h) harvesting said desired portion of said medium containing at least one of cells and tissue, while leaving said remainder of medium containing at least one of cells and tissue in said container, wherein said remainder of medium serves as inoculant for a next culture/harvest cycle;
   i) providing sterile at least one of said culture medium and said additives for the next culture/harvest cycle via said additive inlet means;
   j) repeating steps d), e), f), g), h) and i) a plurality of times until in g) the said contaminants are found or at least one of the cells and tissues which are produced are of poor quality, whereupon the device and its contents are disposed of.

47. The method as claimed in claim 46, wherein said device further comprises air inlet means for introducing sterile air in the form of bubbles into said culture medium through a first inlet opening connectable to a suitable sterile air supply, said method further comprising the step of providing sterile air to said air inlet means during the first and each subsequent cycle.

48. The method as claimed in claim 47, wherein said sterile air is supplied continuously throughout at least one culturing cycle.

49. The method as claimed in claim 47, wherein said sterile air is supplied in pulses during at least one culturing cycle.

50. A method for axenically culturing and harvesting at least one of tissue and a quantity of cells in a battery of disposable devices comprising the steps of:
   a) providing a battery of devices,
      said battery comprising at least two devices, at least one of said devices comprising a sterilisable disposable container which is at least one of transparent and translucent, having a top end and a bottom end, which container may be at least partially filled with at least one of a suitable sterile biological cell culture medium, a suitable sterile biological tissue culture medium, axenic inoculant, sterile air and required other sterile additives, said container comprising:
         (i) gas outlet means for removing at least one of excess air and waste gases from said container;
         (ii) additive inlet means for introducing at least one of said inoculant, said culture medium and said additives into said container;
      and characterized in further comprising
         (iii) reusable harvesting means comprising suitable flow control means for enabling harvesting of at least a desired portion of said medium containing at least one of said tissue and quantity of cells when desired, thereby enabling said device to be used continuously for at least one further consecutive culturing/harvesting cycle, and
         (iv) an air inlet means for introducing sterile air in the form of bubbles into said culture medium through a first inlet opening, wherein said air inlet means is connectable to a suitable air supply,
      wherein a remainder of said medium containing at least one of said cells and tissue, remaining from a previous harvested cycle, may serve as inoculant for a next culture and harvest cycle, wherein at least one of said culture medium and said required additives are provided, and
      said harvesting means of each device is suitably connected to a common harvesting piping having a free end optionally comprising suitable aseptic connecting means thereat and said harvesting means further comprises a contamination prevention means for substantially preventing introduction of contaminants into said container via said common harvesting piping, said contamination prevention means comprising a U-shaped fluid trap, said fluid trap having one arm thereof free and further having an opening and wherein the other end of said contamination prevention means is aseptically mountable to said free end of said common harvesting piping via suitable aseptic connection means
   and for at least one said device thereof:
   b) providing axenic inoculant to said device via said common harvesting piping;
   c) providing sterile at least one of said culture medium and said additives to said device via said common additive inlet piping;

k) optionally illuminating said device with external light means;

l) allowing at least one of said cells and tissue in said device to grow in said medium to a desired yield;

m) allowing at least one of excess air and waste gases to leave said device continuously via said common gas outlet piping;

n) checking for at least one of contaminants and the quality of at least one of the cells and tissues which are produced in said device: if in said device contaminants are found or at least one of the cells and tissues which are produced are of poor quality, said harvesting means of said device is closed off preventing contamination of other said devices of said battery; if in all of said devices of said battery contaminants are found or at least one of the cells and tissues which are produced therein are of poor quality, all the devices and their contents are disposed of; if contaminants are not found and the quality of at least one of the produced cells and tissues is acceptable, the device is considered harvestable and step h) is executed;

o) for each said harvestable device of step g), harvesting said desired portion of said medium containing at least one of cells and tissue via said common harvesting piping and said contamination prevention means to a suitable receiving tank, while leaving said remainder of medium containing at least one of said cells and tissue in said container, wherein said second portion of medium serves as inoculant for a next culture/harvest cycle;

p) providing sterile at least one of said culture medium and said additives for the next culture/harvest cycle via said additive inlet means;

q) repeating steps d), e), f), g), h) and i) a plurality of times until in g) said contaminants are found or at least one of the cells and tissues which are produced are of poor quality for all of said devices of said battery, whereupon said contamination prevention means are disconnected from said common harvesting means and said devices and their contents are disposed of.

51. A method for axenically culturing and harvesting at least one of tissue and a quantity of cells in a battery of disposable devices comprising the steps of:

a) providing a battery of devices,
    said battery of devices comprising at least two disposable devices, at least one of said devices comprising a sterilisable disposable container which is at least one of transparent and translucent, having a top end and a bottom end, which container may be at least partially filled with at least one of a suitable sterile biological cell culture medium, a suitable sterile biological tissue culture medium, axenic inoculant, sterile air and required other sterile additives, said container comprising:
    (i) gas outlet means for removing at least one of excess air and waste gases from said container;
    (ii) additive inlet means for introducing at least one of said inoculant, said culture medium and said additives into said container;
    and characterized in further comprising
    (iii) at least one air inlet means for introducing sterile air in the form of bubbles into said culture medium through a first inlet opening, wherein said air inlet means is suitably connected to a common air inlet piping having a free end optionally comprising suitable aseptic connecting means thereat, which is further connectable to a suitable air supply;
    (iv) reusable harvesting means comprising suitable flow control means for enabling harvesting of at least a desired portion of said medium containing at least one of said tissues and quantity of cells when desired, thereby enabling said device to be used continuously for at least one further consecutive culturing/harvesting cycle, wherein a remainder of said medium containing at least one of said cells and tissue, remaining from a previous harvested cycle, may serve as inoculant for a next culture and harvest cycle, wherein at least one of said culture medium and said required additives are provided;

and for at least one said device thereof:

b) providing axenic inoculant to said device via said common harvesting piping;

c) providing sterile at least one of said culture medium and said additives to said device via said common additive inlet piping;

d) providing sterile air to said device via said common air inlet piping;

e) optionally illuminating said device with external light means;

f) allowing at least one of said cells and tissue in said device to grow in said medium to a desired yield;

g) allowing at least one of said excess air and waste gases to leave said device continuously via said common gas outlet piping;

h) checking for at least one of contaminants and the quality of at least one of the cells and tissues which are produced in said device: if in said device contaminants are found or at least one of the cells and tissues which are produced are of poor quality, said harvesting means of said device is closed off preventing contamination of other said devices of said battery; if in all of said devices of said battery contaminants are found or at least one of the cells and tissues which are produced therein are of poor quality, all the devices and their contents are disposed of; if contaminants are not found and the quality of at least one of the produced cells and tissues is acceptable, the device is considered harvestable and step i) is executed;

i) for each of said harvestable device of step h), harvesting at least a desired portion of said medium containing at least one of said cells and tissue via said common harvesting piping and said contamination prevention means to a suitable receiving tank, while leaving said remainder of medium containing at least one of the cells and tissue in said container, wherein said remainder of medium serves as inoculant for a next culture/harvest cycle;

j) providing sterile at least one of said culture medium and said additives for the next culture/harvest cycle via said additive inlet means;

k) repeating steps d), e), f), g), h), i) and j) a plurality of times until in h) said contaminants are found or at least one of the cells and tissues which are produced are of poor quality for all of said devices of said battery, whereupon said contamination prevention means are disconnected from said common harvesting means and said devices and their contents are disposed of.

52. The method as claimed in claim 46, wherein said remainder of said medium containing at least one of said cells and tissue comprises between about 2.5% and about 45% of the original volume of said culture medium and said inoculant.

53. The method as claimed in claim 52, wherein said remainder of said medium containing at least one of said cells and tissue comprises between about 10% and about 20% of the original volume of said culture medium and said inoculant.

54. The method as claimed in claim 47, wherein said step of providing sterile air further comprises the step of producing air bubbles, some of said air bubbles comprising a mean diameter of between about 1 mm and about 10 mm.

55. The method as claimed in claim 54, wherein at least some of said air bubbles comprise a mean diameter of about 4 mm.

56. The device as claimed in claim 31, wherein said container comprises an internal fillable volume of between about 50 liters and 150 liters.

57. The device as claimed in claim 31, wherein said container comprises an internal fillable volume of about 100 liters.

* * * * *